United States Patent [19]

Hasegawa et al.

[11] Patent Number: 5,278,300
[45] Date of Patent: Jan. 11, 1994

[54] 4,6-O-HYDROXYPHOSPHORYL-GLUCOSAMINE DERIVATIVES

[75] Inventors: Akira Hasegawa, 1735-160, Ohkurayama, Kano, Gifu-shi Gifu-ken 501-31; Shinichi Uesato, Yokohama; Tomio Ishida, Yokohama; Yutaka Saito, Yokohama, Makoto Kiso, Gifu, all of Japan

[73] Assignees: Japan Tobacco, Inc., Tokyo; Akira Hasegawa, Gifu, both of Japan

[21] Appl. No.: 778,094

[22] PCT Filed: Apr. 11, 1991

[86] PCT No.: PCT/JP91/00475

§ 371 Date: Dec. 12, 1991

§ 102(e) Date: Dec. 12, 1991

[87] PCT Pub. No.: WO91/16332

PCT Pub. Date: Oct. 31, 1991

[30] Foreign Application Priority Data

Apr. 12, 1990 [JP] Japan .................................. 2-95024

[51] Int. Cl.⁵ ................ C07H 13/00; C07H 5/06; A61K 31/70
[52] U.S. Cl. ...................... 536/53; 536/55.2; 536/115; 536/117
[58] Field of Search .............. 536/117, 53, 115, 55.2, 536/17.9; 514/62, 25

[56] References Cited

U.S. PATENT DOCUMENTS

| | | | |
|---|---|---|---|
| 4,322,523 | 3/1982 | Wagner | 536/115 |
| 4,323,561 | 4/1982 | Nowotny | 536/53 |
| 4,485,054 | 11/1984 | Mezei et al. | 424/182 |
| 4,746,742 | 5/1988 | Hasegawa et al. | 536/117 |
| 4,818,816 | 4/1989 | Petitou et al. | 514/62 |
| 4,883,665 | 11/1989 | Miyazima et al. | 424/417 |
| 5,032,505 | 7/1991 | Pierce et al. | 536/53 |
| 5,041,427 | 8/1991 | Takayama et al. | 536/117 |
| 5,059,685 | 10/1991 | Conti | 536/55.2 |

FOREIGN PATENT DOCUMENTS

| | | |
|---|---|---|
| 0171710 | 2/1986 | European Pat. Off. . |
| 0192296 | 8/1986 | European Pat. Off. . |
| 0224260 | 6/1987 | European Pat. Off. . |
| 0333490 | 9/1989 | European Pat. Off. . |

(List continued on next page.)

OTHER PUBLICATIONS

Chemical Abstracts, vol. 100, No. 13 (1984), p. 693, 103782u.

(List continued on next page.)

*Primary Examiner*—Johnnie R. Brown
*Assistant Examiner*—Everett White

[57] ABSTRACT

4,6-O-hydroxyphosphoryl-glucosamine derivatives as shown in the following formula [I] and their pharmaceutically-acceptable salts:

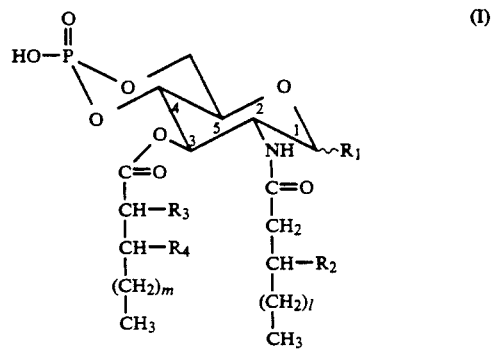

wherein $R_1$ and $R_2$ represent a hydrogen atom or a hydroxy group; one of $R_3$ and $R_4$ represents $-O-CO(CH_2)_nCH_3$, $-CH_2(CH_2)_nCH_3$, or $-O-CH_2(CH_2)_nCH_3$, and the other represents a hydrogen atom; l is an integer of 4–16; m is an integer of 4–16; and n is an integer of 6–18.

6 Claims, No Drawings

FOREIGN PATENT DOCUMENTS

| | | |
|---|---|---|
| 0335597 | 10/1989 | European Pat. Off. |
| 0346472 | 12/1989 | European Pat. Off. |
| 60-7934 | 1/1985 | Japan |
| 60-501259 | 8/1985 | Japan |
| 61-126093 | 6/1986 | Japan |
| 61-126094 | 6/1986 | Japan |
| 61-172867 | 8/1986 | Japan |
| 61-227586 | 10/1986 | Japan |
| 61-246195 | 11/1986 | Japan |
| 61-275299 | 12/1986 | Japan |
| 62-36306 | 2/1987 | Japan |
| 62-129292 | 6/1987 | Japan |
| 63-30495 | 2/1988 | Japan |
| 63-44588 | 2/1988 | Japan |
| 63-333391 | 2/1988 | Japan |
| 63-77824 | 4/1988 | Japan |
| 63-179885 | 7/1988 | Japan |
| 64-52793 | 2/1989 | Japan |
| 1-146891 | 6/1989 | Japan |
| 1-146892 | 6/1989 | Japan |
| 1-175944 | 7/1989 | Japan |
| 1-213290 | 8/1989 | Japan |
| 2-25494 | 1/1990 | Japan |
| 2-62889 | 3/1990 | Japan |
| 262888 | 3/1990 | Japan |
| 3264594 | 11/1991 | Japan |

OTHER PUBLICATIONS

Chem. Abstr. 11th Collective Index, vols. 96–105, 1982–1986.

Formula $C38H73N07$; Formula $C73H117N08$.

Chemical Abstracts, vol. 107, No. 5 (1987) p. 402, 46060a.

Chemical Formula Index, vol. 107, (1987), Formula $C24H47N06$.

Japanese Bacteriology Journal 40 (1) 57 1985.

Proc. Natl. Acad. Sci., USA vol. 80 pp. 4624–4628, (1983).

Anderson et al. (1983) Bact. Lipp. 231:255–75.

Drug Delivery System (1987) vol. 2, No. 1, pp. 41–51.

Eur. J. Biochem. 47 (1974) pp. 179–185.

Journal of the Neurological Sciences (1977) 31:173–179.

Chemistry Letters (1980) CMLTAG 11:1373–1376.

Japanese Patent Disclosure (Kokai) No. 2–62889 (1990).

Japanese Patent Disclosure (Kokai) No. 2–25494 (1990).

Japanese Patent Disclosure (Kokai) No. 1–213290 (1989).

Journal of the Chemical Society, Part IV, issued Nov. 1954, Baddeley et al., "Sugar Phosphates Part I Derivatives of Glucose 4:6-(Hydrogen Phosphate)" pp. 3826–3830.

English Language Abstract of JP-1238537.

English Language Abstract of JP-63211222.

English Language Abstract of JP-61050912.

4,6-O-HYDROXYPHOSPHORYL-GLUCOSAMINE DERIVATIVES

TECHNICAL FIELD

The present invention relates to novel 4,6-O-hydroxyphosphoryl-glucosamine derivatives and pharmaceutically-acceptable salts thereof.

The compounds of the present invention exhibit lipid A-like activity, and are useful as pharmaceutical drugs such as immunopotentiation agents and anti-tumour agents.

BACKGROUND ART

Surface layers of Gram-negative bacteria are composed of a cell membrane, a cell wall peptidoglycan, and an outer membrane. The outer membrane contains lipopolysaccharides (hereinafter abbreviated LPS). LPS is a main ingredient of endotoxin which induces endotoxin shock, and consists of an acidic protein component, a high-molecular weight polysaccharide component, and a phospholipid component.

LPS induces various morbid conditions such as pyrogenesis, bleeding, arthritis, and encephalomyelitis. LPS is also known to exhibit a host protection effect on immune-activating mechanisms such as macrophage-activation, B-cell blastogenesis activity, and cell-mediated immunity-activation, as well as antitumour effects such as IFN(interferon) induction and TNF(tumour necrosis factor) induction.

The main component of LPS which exhibits these activities among said three components is the phospholipid component, which is called lipid A. Lipid A comprises a fatty acid residue and phosphoric acid, both of which are combined with a disaccharide amine, and has the following formula [Japanese Bacteriology Journal 40(1), 57(1985) and Proc. Natl. Acad. Sci. U.S.A. 80, 4624(1983)]:

Lipid A of E coli

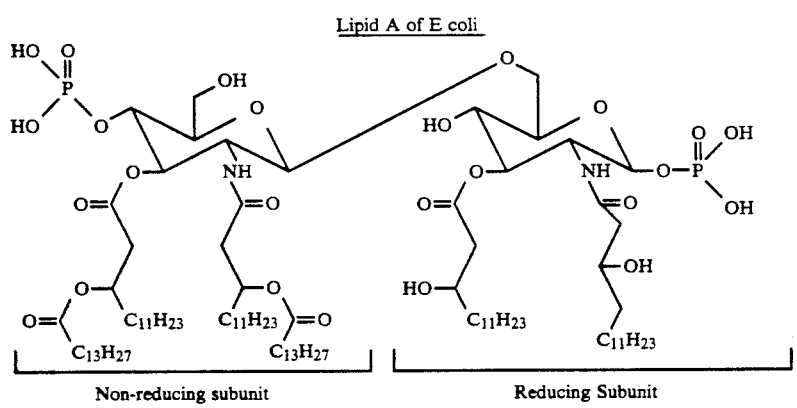

A recent study has revealed that either the non-reducing subunit or the reducing subunit alone as shown above can exhibit the lipid A-like activity, and various analogues have been synthesized based on this finding. Examples of such analogues are disclosed in European Patent Application Disclosure No. 224260, Japanese Patent Application Disclosure No. 62888/90, and Japanese Patent Application Disclosure No. 25494/90, etc.

As described above, extensive studies have been conducted in order to obtain lipid A analogues, specifically by modifying them with various substituents and by changing introduced substituent sites. However, no lipid A analogue has been developed which is pharmaceutically applicable, mainly because the same substituent exhibits different activities depending on its introduced site, thus making the study of pharmaceutical applications of the lipid A-like analogues difficult. Therefore, lipid A analogues of higher activity and lower toxicity are expected to be developed.

DISCLOSURE OF INVENTION

The object of the present invention is to produce novel compounds which exhibit more effective lipid A-like activity and low toxicity.

The inventors of the present invention have been energetically studied lipid A derivatives in order to attain said object. As a result, the inventors have discovered novel compounds which exhibit strong lipid A-like activity such as mitogenic activity of varying strength depending on the analogue, TNF-inducing activity, and IFN-inducing activity, and which nevertheless exhibit low toxicity, and have completed the present invention based on these findings.

Novel 4,6-O-hydroxyphosphoryl-glucosamine compounds according to the present invention have the following general formula (I):

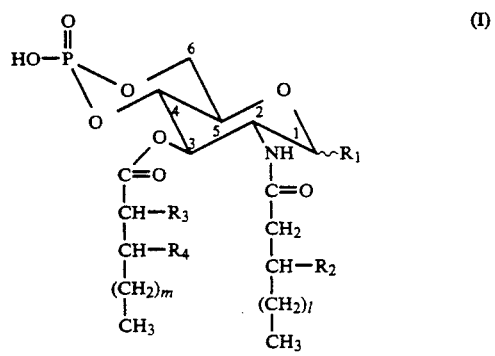

wherein $R_1$ and $R_2$ represent a hydrogen atom or a hydroxy group; one of $R_3$ and $R_4$ is $-OCO(CH_2)_nCH_3$, $-CH_2(CH_2)_nCH_3$, or $-O-CH_2(CH_2)_nCH_3$, and the other is a hydrogen atom; $l$ is an integer of 4–16; $m$ is an integer of 4–16; and $n$ is an integer of 6–18.

This invention also relates not only to said compounds but also to their pharmaceutically-acceptable salts. Examples of these salts are inorganic alkali metal salts, alkali-earth metal salts, and organic amine salts. Specifically, salts of the compounds with sodium, potassium, lithium, calcium, triethanolamine, diethanolamine, monoethanolamine, triethylamine, etc. are exemplified.

4,6-O-hydroxyphosphoryl-glucosamine derivatives (I) according to the present invention have two structural characteristics as follows. First, the pyranose ring is acylated at the 3-position with α- or β-alkylated fatty acids, α- or β-alkoxylated fatty acids, or α- or β-acyloxylated fatty acids. Second, hydroxyphosphoryl groups [>P(O)OH] are introduced to the 4- and 6-positions of the pyranose ring. The present compounds [I] are expected to be useful by virtue of these characteristics as pharmaceutical drugs such as immune-activating agents. The present invention also includes all stereoisomers of the compounds (I) and a mixture thereof.

These compounds (I) can be produced according to the following reaction steps:

FLOW 1

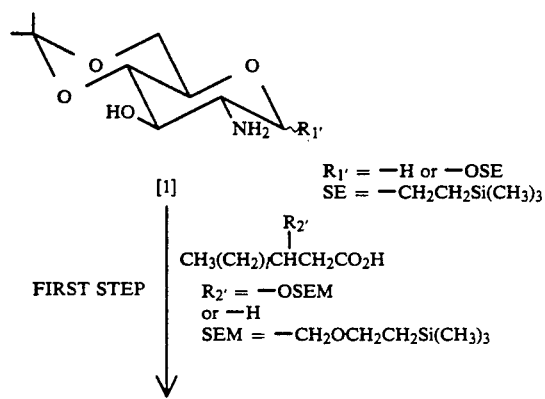

$R_{1'} = $ —H or —OSE
$SE = $ —CH$_2$CH$_2$Si(CH$_3$)$_3$

[1]

FIRST STEP $$CH_3(CH_2)_l\overset{R_{2'}}{\underset{|}{C}H}CH_2CO_2H$$

$R_{2'} = $ —OSEM
or —H
$SEM = $ —CH$_2$OCH$_2$CH$_2$Si(CH$_3$)$_3$

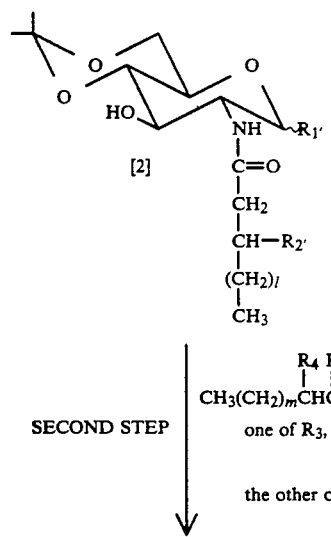

[2]

SECOND STEP $$CH_3(CH_2)_m\overset{R_4}{\underset{|}{C}H}\overset{R_3}{\underset{|}{C}H}CO_2H$$

one of $R_3$, $R_4$ is —OCO(CH$_2$)$_n$CH$_3$,
 —CH$_2$(CH$_2$)$_n$CH$_3$ or
 —OCH$_2$(CH$_2$)$_n$CH$_3$;
the other of them is Hydrogen

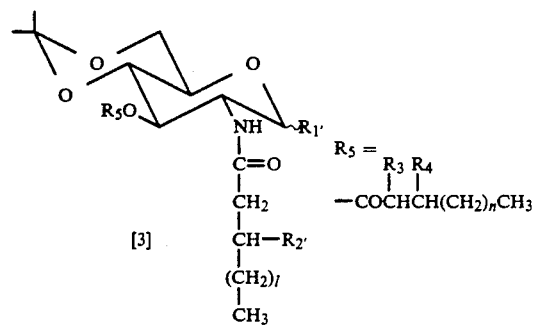

[3]

$R_5 = \overset{R_3\ R_4}{\underset{|\ \ |}{-COCHCH(CH_2)_nCH_3}}$

-continued
FLOW 1

THIRD STEP

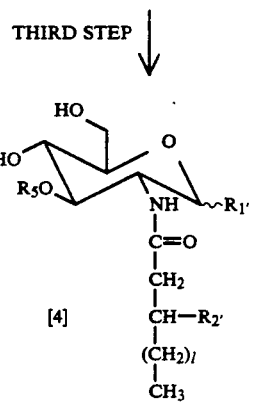

[4]

FOURTH STEP

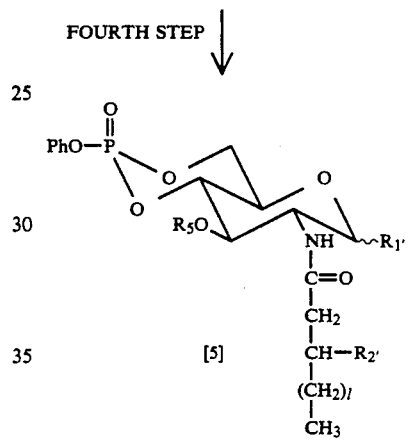

[5]

FIFTH STEP ($R_{1'} = $ —H and
$R_{2'} = $ —H)

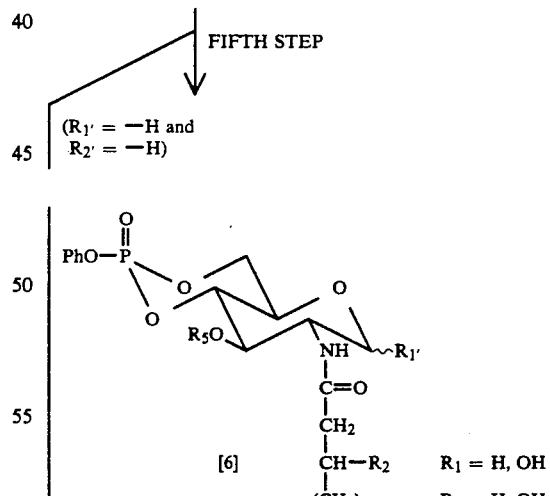

[6]    $R_1 = $ H, OH
    $R_2 = $ H, OH

SIXTH STEP

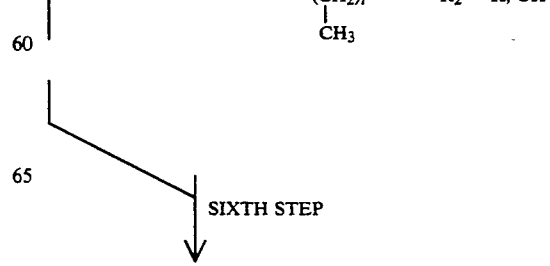

-continued
FLOW 1

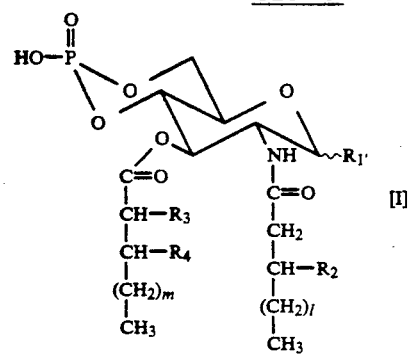

A description of said flow 1 in detail is as follows:

The First Step

Known compound [1] derived from D-glucosamine (see Japanese Patent Disclosure No. 197582/86) is amidated to form an amide compound [2]. This procedure is performed by reacting compound [1] with a fatty acid compound whose hydroxyl group at the 3-position is protected with a 2-(trimethylsilyl)ethoxymethyl group (—SEM group) or with a straight-chain fatty acid compound having no hydroxy group, in an inert solvent such as dichloromethane, in the presence of a condensation agent such as dicyclohexylcarbodiimide (DCC) and 1-ethyl-3(3-dimethylaminopropyl)-carbodiimide hydrochloride (WSC·HCl).

The Second Step

Compound [2] obtained in the first step is reacted with an acylating agent, thereby acylating the hydroxyl group at the 3-position of the ring in order to obtain compound [3]. Examples of the acylating compound are an α- or β-alkyl fatty acid, an α- or β-acyloxy fatty acid or an α- or β-alkoxy fatty acid ($R_5OH$). This step is performed in a solvent such as dichloromethane in the presence of a catalytic amount of dimethylaminopyridine (DMAP), and a condensation agent such as DCC and WSC·HCl.

The Third Step

Compound [3] obtained in the second step is hydrolyzed with an acid such as acetic acid in order to eliminate the protection groups at the 4- and 6-positions, yielding compound [4].

The Fourth Step

Compound [4] is made to react with phenyl dichlorophosphate in an inert solvent such as dichloromethane in the presence of a base such as pyridine and DMAP in order to obtain compound [5].

The Fifth Step

This step is performed in order to eliminate protection groups at the hydroxy groups when $R_1'$ and/or $R_2'$ are protected hydroxy groups. Therefore, when both $R_1'$ and $R_2'$ are hydrogen atoms, this step is not required. When both $R_1'$ and $R_2'$ are protected hydroxy groups, both protection groups may be simultaneously eliminated, or they may be separately eliminated in a stepwise manner.

The elimination step can be performed in various known manners. For example, when the $R_1'$ and/or $R_2'$ of the compound [5] are —OSE, compound [5] is dissolved in an inert solvent such as dichloromethane, and an acid such as boron trifluoride etherate ($BF_3 \cdot OEt_2$) or a fluoride ion generating agent such as tetrabutylammonium fluoride is added to the solution in order to easily eliminate the protection groups.

It is noted that the protection groups in the $R_1'$ and/or $R_2'$ positions are not restricted to —OSE described above, but they may be, for example, benzyl groups (—Bn group). When they are benzyl groups, they are easily eliminated through catalytic hydrogenation in the presence of a catalyst such as platinum and palladium.

The Sixth Step

Compound [6] is hydrogenated over platinum dioxide ($PtO_2$), etc. in a solvent such as ethanol, methanol, and acetic acid to yield the objective compound (I).

This objective compound (I) can be also prepared according to the following reaction scheme from a lipid A analogue obtained in a known manner.

FLOW 2

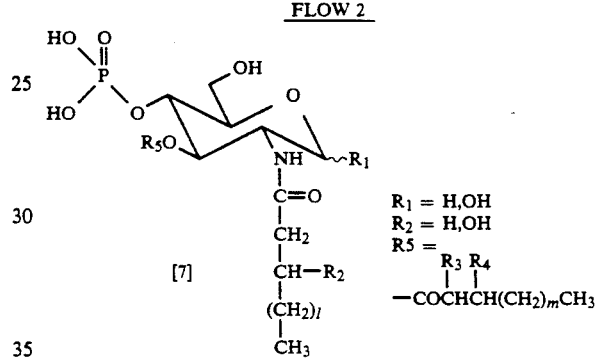

$R_1 = H, OH$
$R_2 = H, OH$
$R_5 = $
$\quad \overset{R_3}{|} \overset{R_4}{|}$
$-COCHCH(CH_2)_m CH_3$

↓ SEVENTH STEP

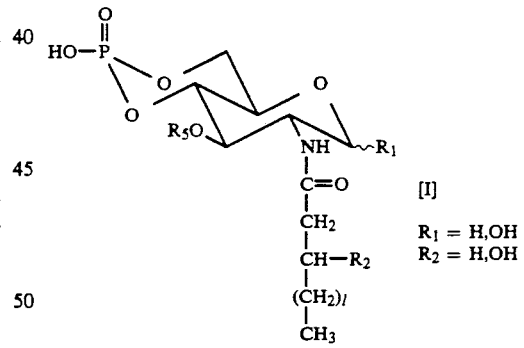

$R_1 = H, OH$
$R_2 = H, OH$

This flow 2 comprises the following seventh step.

The Seventh Step

Compound [7] (for example, see Japanese Patent Disclosure No. 62888/90) is made to react with a condensation agent such as DCC and WSC·HCl in a solvent such as tetrahydrofuran(THF), dichloromethane, and chloroform. By this reaction, compound [7] is cyclized by intramolecular condensation to yield the objective compound (I).

Among α- or β-alkylated fatty acids, α- or β-acyloxylated fatty acids, and α- or β-alkoxylated fatty acids, some are known, and others are easily prepared from known compounds. Examples of methods for producing these substituents are as follows:

Method for Producing α-alkylated fatty acid

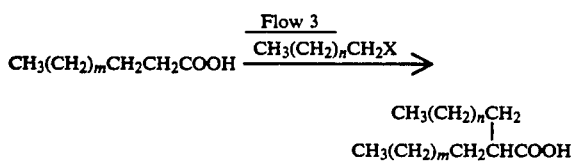

wherein X represents a halogen atom.

This reaction is performed in aprotic solvents such as tetrahydrofuran (THF) containing hexamethylphosphoric triamide (HMPA), etc. First, a straight chain carboxylic acid having the corresponding number of carbons is added with two equivalents of strong base such as lithium diisopropylamide (LDA) in order to form the dianion of the carboxylic acid. Next, the dianion is reacted with a straight chain alkylhalide having the corresponding number of carbons to obtain the α-alkylated fatty acid.

Method for Producing β-alkylated fatty acid

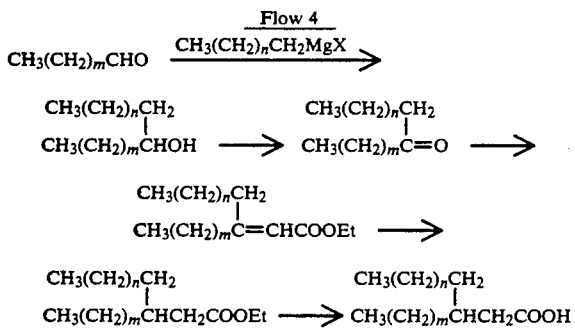

A straight chain alkyl halide having the corresponding number of carbons is reacted with metal magnesium in an aprotic solvent such as THF in order to form a Grignard reagent. The straight chain aldehyde having the corresponding number of carbons is reacted with the Grignard reagent to yield a secondary alcohol. This alcohol is oxidized with an oxidizing agent such as pyridinium chlorochromate (PCC) and Jones reagent in an inert solvent such as dichloromethane to form a ketone.

Separately, triethyl phosphonoacetate is added with a base such as sodium hydride in order to form a carboanion.

The Wittig reaction of the carboanion and the aforementioned ketone yields an α, β-unsaturated ester.

Next, this ester is subjected to hydrogenation in a solvent such as ethyl acetate in the presence of palladium carbon to form a saturated ester. Finally, this ester is hydrolyzed in a solvent such as aqueous ethanol in the presence of a base such as potassium hydroxide to obtain a β-alkylated fatty acid.

Method for Producing α- or β-acyloxylated fatty acid

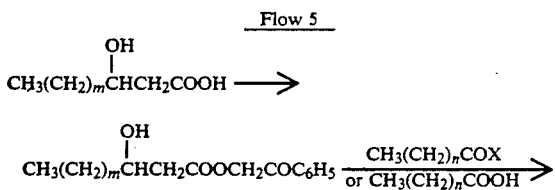

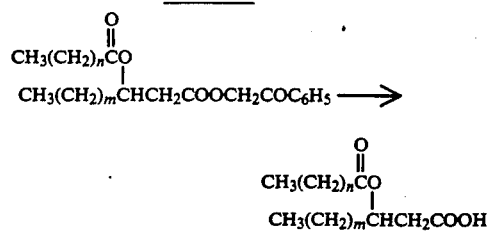

A straight chain 2- or 3-hydroxycarboxylic acid having the corresponding number of carbons (for example, a 3-hydroxycarboxylic acid is shown in flow 5) is acylated as follows. First, the hydroxycarboxylic acid is reacted with phenacyl bromide in a solvent such as ethyl acetate in the presence of a base such as triethylamine to form phenacyl ester. The hydroxy group at the 2- or 3-position of the phenacyl ester is acylated by being reacted with an acid chloride having the corresponding number of carbons in the presence of a base such as pyridine, or with a straight chain carboxylic acid having the corresponding number of carbons in the presence of a condensation agent such as DCC and WSC·HCl in an inert solvent such as dichloromethane. Next, the acylated phenacyl ester is treated with zinc powder and acetic acid in order to eliminate the phenacyl group. As a result, α- or β-acyloxylated fatty acids are obtained.

Method for Producing α- or β-alkoxylated fatty acid

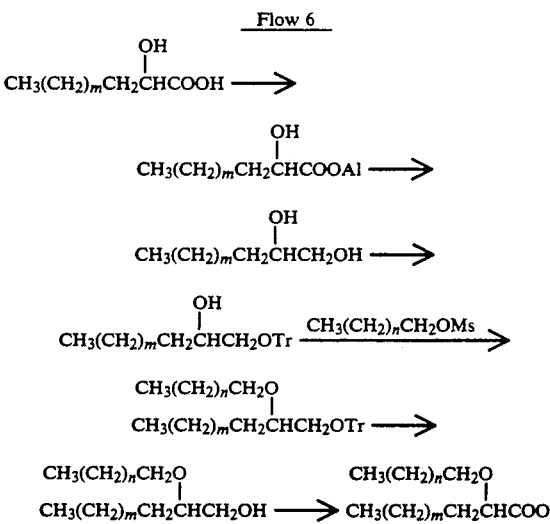

wherein Al indicates an alkyl group such as a methyl group or an ethyl group, Tr indicates a protection group such as a trityl group for a hydroxyl group, and Ms indicates a mesyl group or a tosyl group, etc.

a 2- or 3-hydroxycaroboxylic acid having the corresponding number of carbons (for example, a 2-hydroxycarboxylic acid is shown in flow 6) is esterified with methyl iodide, ethyl iodide or the like in an aprotic solvent such as benzene in the presence of a base such as 1,8-diazabicyclo[5,4,0]7-undecene (DBU). The obtained ester is reduced with a reducing agent such as lithium aluminium hydride in a solvent such as THF to yield a diol. Next, of the —OH groups in the obtained diol, only the primary OH group is selectively protected with a protection group such as a trityl group. The protected alcohol is reacted with a straight chain alcohol which has the corresponding number of carbons and which is mesylated or tosylated, in an aprotic solvent such as THF, in the presence of a base such as potassium hydride or sodium hydride and a phase transfer catalyst such as tetra-n-butylammonium iodide, to introduce an alkoxy substituent. Next, the protection group (trityl group) at the primary hydroxy group is eliminated by using an acid such as p-toluenesulfonic acid. Finally, the obtained alcohol is oxidized with an oxidizing agent such as Jones reagent and PCC in order to obtain a $\beta$-alkoxy substituted fatty acid.

A description of the pharmaceutical applications of the compounds according to the present invention is as follows.

A compound of formula (I) is generally administered systemically, topically, orally, or parenterally.

Although the administered dose varies with the age, weight, and symptoms of the patient in question, the therapeutic effect desired, the route of administration, the treatment period, etc., 0.01–100mg of the compound is generally administered orally or parenterally to an adult, once to several times a day.

Solid compositions prepared to be orally administered according to the present invention include tablets, powder, granules, etc. These solid compositions are obtained by mixing at least one active substance with at least one inert diluent or dispersing agent. Examples of such diluents or dispersing agents include lactose, mannitol, glucose, hydroxypropylcellulose, crystalline cellulose, starch, polyvinylpyrrolidone, magnesium alumino-metasilicate, etc. Other than these diluents or dispersing agents, absorbents such as anhydrous silica powder, etc. may be mixed with compound (I). Further, the solid compositions may contain additives other than inactive diluents, according to generally known methods.

The tablets or pills noted above may be coated, if desired, with acid soluble films or enteric coating films such as saccharose, gelatin, hydroxypropylcellulose or hydroxypropylmethylcellulose phthalate. Tablets or pills may be coated, if desired, with two or more these films. Also, powders or granules may be encapsulated within capsules made of gelatin, ethylcellulose, etc.

Examples of liquid compositions for oral administration include pharmaceutically acceptable emulsions, solutions, suspensions, syrups, elixirs, etc. These liquid compositions may contain conventional inert diluents, e.g., purified water, ethanol, vegetable oils, and emulsifying agents. Further, auxiliary agents such as moisturizing agents or suspending agents, edulcorants, flavouring agents, perfumes, and antiseptics may be contained in the compositions.

Injectable preparations for parenteral administration may contain sterilized aqueous or non-aqueous solvents, solubilizing agents, suspending agents, and emulsifying agents. Examples of the aqueous solvents, solubilizing agents, and suspending agents include distilled water for injection, saline solution, cyclodextrin and its derivatives, organic amines such as triethanolamine, diethanolamine, monoethanolamine, and triethylamine, and inorganic alkalines.

Examples of non-aqueous solvents include propyleneglycol, polyethyleneglycol, vegetable oils such as olive oil, and alcohols such as ethanol. Examples of non-aqueous solubilizing agents include surfactants (which form mixed miscelles) such as polyoxyethylene hydrogenated castor oil, sucrose fatty acid ester, lecithin, and hydrogenated lecithin (which forms liposomes), etc. Emulsion preparations are also included in the non-aqueous solution preparation, which are obtained by using non-aqueous solvents such as vegetable oils with emulsifying agents such as lecithin, polyoxyethylene hydrogenated castor oils, and polyoxyethylenepolyoxypropyleneglycol.

Examples of other compositions which are administered via any route other than per os are topical solutions, liniments such as ointments, suppositories, pessaries, etc., each of which contains at least one active substance and is prepared according to the presently disclosed method.

Hereinafter are described pharmacological actions of the compounds according to the present invention by way of experimental examples. The compounds according to the present invention have shown significant effects in various tests such as IL-1-producing activity, and have also exhibited low toxicities in tests such as the local Schwartzman reaction, and pyrogenicity. Some pharmacological activities of the compounds of the present invention are as follows.

EXPERIMENTAL EXAMPLE 1 ($O_2^-$ PRODUCTION STIMULATING ACTIVITY IN NEUTROPHILS)

$O_2^-$ - production stimulating activity in neutrophils was evaluated utilizing the following experimental system [see J. Exp. Med., 160, 1656–1671. (1984)]. To the peritoneal cavity of C3H/HeN mice (male, 8–9 weeks old), physiological saline containing 0.2% (w/v) casein was administered. Three hours later, peritoneal exudate cells (90% or more of which are neutrophils) were collected. These cells ($1.7 \times 10^6$ cells/ml/tube) were incubated in the presence of the compound (10 $\mu$g/ml) according to the present invention at 37° C. for 60 minutes. After addition of 80 $\mu$M of cytochrome C and 0.1 $\mu$M of formyl-methionyl-leucylphenylalanine (FMLP), the mixture was incubated in the presence of or in the absence of superoxide dismutase (SOD) at 37° C. for 10 minutes. Then, SOD-inhibitable cytochrome C reduction was estimated from the difference between the absorbances at 550 nm and 541.7 nm, and from the molar absorption coefficient ($16.5 \times 10^3$). $O_2^-$ production-stimulating activity in terms of Stimulation % was calculated according to the following formula:

$$\text{Stimulation (\%)} = \frac{\text{the amount of } O_2^- \text{ produced in the presence of the compound according to the invention}}{\text{the amount of } O_2^- \text{ produced in the absence of the compound according to the invention}} \times 100 - 100$$

The compound according to the present invention exhibited the activity shown in Table 1. The control compound in the Table 1 is 2-deoxy-2[(3R)-3-hydroxytetradecanamide]-4-O-phosphono-3-O-[(3R)-3-tetradecanoyloxytetradecanoyl]-D-glucopyranose (GLA-60).

TABLE 1

| | Stimulation (%) | |
|---|---|---|
| Compound | Experiment 1 | Experiment 2 |
| No compound | 0 | 0 |
| Control | 60 | 60 |
| Example 1 | 55 | — |

TABLE 1-continued

| Compound | Stimulation (%) | |
|---|---|---|
| | Experiment 1 | Experiment 2 |
| Example 4 | — | 55 |

EXPERIMENTAL EXAMPLE 2 (TNF-PRODUCING ACTIVITY)

TNF-producing activity was evaluated utilizing the following experimental system.

The first stimulating agent, 5% *Corynebacterium parvum* suspension (0.2 ml physiological saline solution), was intravenously administered to ICR mice (female, 6–7 week-aged). Nine days later, the second stimulating agent, the compound of the present invention, was intravenously administered to the same mice at 10 μg/mice. In 90 minutes, 0.5–1 ml of blood was taken from the retro orbital plexus. The obtained blood was allowed to clot at room temperature for five to six hours, and centrifuged at 7200×g for five minutes to separate the serum. The obtained serum was incubated at 56° C. for 30 minutes for inactivation before use in the following experiment.

TNF activity in the serum was measured via a cytotoxicity assay employing L929 cells. L929 cells were prepared in a concentration of $6 \times 10^4$ cells/well (0.1 ml) RPMI 1640 medium containing 10% FBS (fetal bovine serum) and 2 μg/ml actinomycin D in 96-well plates. Serial dilutions of the obtained serum in RPMI 1640 medium containing 10% FBS were added to each well in the plate (0.1 ml/well). After 48 hours incubation at 37° C., the viable cells were fixed with methanol. These cells were then stained with 0.2% crystal violet, and the dye was extracted with 1% SDS (sodium dodecyl sulphate). Next, the absorbance at 550 nm was measured. Finally, the cytotoxicity ratio (%) was calculated according to the following formula, and the reciprocal of the dilution of the serum showing 50% cytotoxicity was determined for the TNF titer in the serum (U/ml).

Cytotoxicity (%) =
[OD$_{550}$ (medium alone) − OD$_{550}$ (serum obtained by administering compounds of the invention)] ×
100/OD$_{550}$ (medium alone)

The compounds of the present invention exhibited the activities shown in Table 2.

TABLE 2

| Compound | The Amount of TNF in the Serum (U/ml) | |
|---|---|---|
| | Experiment 1 | Experiment 2 |
| No compound | <10 | <10 |
| Control | 158000 | 80000 |
| Example 1 | 133000 | — |
| Example 2 | — | 102000 |

EXPERIMENTAL EXAMPLE 3 (MITOGEN ACTIVITY)

The mitogen activity of the compounds according to the present invention was evaluated by utilizing the following experimental system [see Eur. J. Immunol., 14, 109–114. (1984)].

The spleens of C3H/HeN mice (males, 6–10-weeks old) were isolated in an aseptic manner. The spleen tissue was loosened in Dulbecco's modified Eagle medium (DMEM) and then subjected to a stainless mesh in order to filter the spleen cells. Next, erythrocytes contained in the collected cells were hemolyzed, and the obtained cells were suspended in RPMI 1640 medium containing 5% FBS for subsequent use.

Evaluation of mitogenic activity of the compounds according to the present invention was conducted by measuring the amount of $^3$H-thymidine incorporated into the cells during culturing of the cells which were treated with the compounds according to the present invention. First, the spleen cells were transferred to a 96-well plate at $5 \times 10^5$ cells/well (100 μl). To each well, the compound according to the present invention at a given concentration (100 μl) was added, and the obtained solution in each well was cultured under 5% CO$_2$ at 37° C. for 48 hours. After that, $^3$H-thymidine was added at 1 μCi/well (50 μl), followed by culturing for four hours. The obtained cells were washed with phosphate buffered saline (PBS), and the amount of $^3$H-thymidine incorporated into the cells (the amount of radioactivity) was determined using a liquid scintillation counter. The result was shown by calculating the following Stimulation Index:

$$\text{Stimulation Index} = \frac{\begin{array}{c}\text{The Radioactive Amount when the}\\\text{compound is added to the medium (cpm)} -\\\text{The Radioactive Amount when the}\\\text{medium only is added (cpm)}\end{array}}{\begin{array}{c}\text{The Radioactive Amount when the}\\\text{medium only is added (cpm)}\end{array}}$$

The compounds according to the present invention exhibited the following activities.

TABLE 3

| Compound | Stimulation Index | |
|---|---|---|
| | Experiment 1 | Experiment 2 |
| No compound | 0 | 0 |
| Control | 15.8 | 8.4 |
| Example 1 | 32.1 | — |
| Example 4 | — | 20.7 |

EXPERIMENTAL EXAMPLE 4 (COLONY STIMULATING FACTOR-INDUCING ACTIVITY)

By utilizing the following experimental protocol, in vivo colony stimulating factor (CSF) inducing activity of the compounds according to the present invention was evaluated [see Immunology, 21, 427–436. (1971)].

5 μg of the present compounds according to the present invention were administered to the caudal vein of C57BL mice (male, 8–10-weeks old). After six hours, the blood was sampled from the plexus venous orbitalis of said mice. This blood was allowed to stand at 4° C. for two hours for sufficient coagulation, and then centrifuged at 1500×g. The resultant supernatant solution was collected for use as a CSF-containing serum sample.

Separately, from the femora of mice which were the same series as the mice used for sampling the serum, the bone marrow cells were sampled. Specifically, both ends of the femora isolated in an aseptic manner were cut, and an injection needle was inserted into one end to aspirate the bone marrow cells into a culture solution (DMEM). The obtained cell suspension was sufficiently stirred, washed with the culture solution several times, and suspended in the culture solution again.

Next, the cell culture prepared as described was adjusted to a final concentration of $10^5$cells/ml by utilizing a medium (DMEM) containing 0.3% agar, 25% horse serum, and 50 μM 2-mercaptoethanol. To this solution, 0.1 ml of said serum sample which had been diluted to ⅓ with said DMEM medium was added, and the obtained solution was transferred to a culture plate of 35 mm diameter. Then, the resultant culture solution was cultured under 7% $CO_2$ at 37° C. for seven days to form colonies. Colonies as containing at least 20 unseparated cells were counted, and the numbers thus obtained were taken as indicating the CSF inducing activity of the compounds according to the present invention.

This activity is shown in the following Table 4.

TABLE 4

| Compound | The Number of Colony Formed/ The number of Bone Marrow Cells ($10^5$) | |
|---|---|---|
| | Experiment 1 | Experiment 2 |
| No compound | 0 | 0 |
| Control | 89 | 53 |
| Example 1 | 153 | — |
| Example 4 | — | 66 |

EXPERIMENTAL EXAMPLE 5 (LETHAL TOXICITY IN GALACTOSAMINE-SENSITIZED MICE)

Lethal toxicity in galactosamine-sensitized mice was evaluated by utilizing the following experimental system [see J. Biochem., 98, 395–406. (1985)].

To C57BL mice (male, 7-weeks old), 10 mg/mouse of D-galactosamine/HCl was intraperitoneally administered. Immediately after that, the compound of this invention was intravenously administered. After these administrations, the general condition of the mice were observed every one hour for seven hours, and every day from the following day to the seventh day.

The compound of the present invention exhibit lethal toxicity as shown in the following Table 5;

TABLE 5

| Compound | $LD_{50}$ (galactosamine load) (μg/kg) |
|---|---|
| Lipid A | 0.3 |
| Control | 3.0 |
| Example 1 | 31.3 |
| Example 4 | 71.1 |

*Synthetic lipid A (LA-15-PP, 506, manufactured by Daiichi Kagaku Yakuhin)

BEST MODE OF CARRYING OUT THE INVENTION

Hereinafter is a detailed description of methods for producing the final objective compound (I) and its intermediates [1] to [7] by way of examples. However, it should be understood that the present invention is not restricted to these examples. For example, the following compounds are also included in the present invention.

1,5-anhydro-2-deoxy-2-dodecanamido-3-O-{(2RS)-2-hexadecyloxydodecanoyl}-4,6-O-hydroxyphosphoryl-D-glucitol 1,5-anhydro-2-deoxy-2-dodecanamido-3-O-{(3RS)-3-hexadecyloxydodecanoyl}-4,6-O-hydroxyphosphoryl-D-glucitol 1,5-anhydro-2-deoxy-3-O-{(3RS)-3-dodecylhexadecanoyl}-2-hexadecanamido-4,6-O-hydroxyphosphoryl-D-glucitol 1,5-anhydro-2-deoxy-3-O-{(2RS)-2-dodecyloxyoctadecanoyl}-2-{(3R)-3-hydroxydodecanamido}-4,6-O-hydroxyphosphoryl-D-glucitol 1,5-anhydro-3-O-{(3RS)-3-decyloctadecanoyl}-2-deoxy-2-{(3RS)-3-hydroxyhexadecanamido}-4,6-O-hydroxyphosphoryl-D-glucitol 1,5-anhydro-2-deoxy-2-dodecanamido-3-O-{(2RS)-2 dodecyloxyoctadecanoyl}-4,6-O-hydroxyphosphoryl-D-glucitol 1,5-anhydro-3-O-{(3RS)-3-decyloctadecanoyl}-2-deoxy-2-hexadecanamido-4,6-O-hydroxyphosphoryl-D-glucitol 2-deoxy-3-O-{(2RS)-2-dodecylhexadecanoyl}-4,6-O-hydroxyphosphoryl-2-tetradecanamido-D-glucopyranose 2-deoxy-4,6-O-hydroxyphosphoryl-2-tetradecanamido-3-O-{(2RS)-2tetradecanoyloxytetradecanoyl}-D-glucopyranose 2-deoxy-3-O-{(2RS)-2-dodecyloxyhexadecanoyl}-4,6-O-hydroxyphosphoryl-2-tetradecanamido-D-glucopyranose 2-deoxy-3-O-{(3RS)-3-dodecylhexadecanoyl}-4,6-O-hydroxyphosphoryl-2-tetradecanamido-D-glucopyranose 2-deoxy-4,6-O-hydroxyphosphoryl-2-tetradecanamido-3-O-{(3RS)-3-tetradecanoyloxytetradecanoyl}-D-glucopyranose 2-deoxy-3-O-{(3RS)-3-dodecyloxyhexadecanoyl}-4,6-O-hydroxyphosphoryl-2-tetradecanamido-D-glucopyranose 2-deoxy-3-O-{(3RS)-3-dodecyloxyhexadecanoyl}-2-{(3RS)-3-hydroxyoctadecanamido}-4,6-O-hydroxyphosphoryl-D-glucopyranose The relationship among the compound (I) according to the present invention, intermediates [1] to [7] for producing the compound (I), and compound numbers are shown in the following Table 6.

TABLE 6

| $R_1$ | $R_2$ | 1 | $R_3$ | $R_5$ $R_4$ | m | COMPOUND NUMBER | | | | | | | (I) | Example |
|---|---|---|---|---|---|---|---|---|---|---|---|---|---|---|
| | | | | | | 1 | 2 | 3 | 4 | 5 | 6 | 7 | | |
| H | OH | 10 | —OCO(CH$_2$)$_{12}$CH$_3$ | H | 10 | 1a | 2a | 3a | 4a | 5a | 6a | | A | 1 |
| H | OH | 8 | —OCO(CH$_2$)$_{10}$CH$_3$ | H | 12 | 1a | 2b | 3b | 4b | 5b | 6b | | B | 2 |
| H | OH | 12 | —OCO(CH$_2$)$_{14}$CH$_3$ | H | 8 | 1a | 2c | 3c | 4c | 5c | 6c | | C | 3 |
| H | OH | 10 | —CH$_2$(CH$_2$)$_{12}$CH$_3$ | H | 10 | 1a | 2a | 3d | 4d | 5d | 6d | | D | 4 |
| H | OH | 8 | —CH$_2$(CH$_2$)$_{14}$CH$_3$ | H | 10 | 1a | 2b | 3e | 4e | 5e | 6e | | E | 5 |
| H | OH | 12 | —CH$_2$(CH$_2$)$_{14}$CH$_3$ | H | 8 | 1a | 2c | 3f | 4f | 5f | 6f | | F | 6 |
| H | OH | 10 | H | —OCO(CH$_2$)$_{12}$CH$_3$ | 10 | 1a | 2a | 3g | 4g | 5g | 6g | | G | 7 |
| H | OH | 10 | H | —CH$_2$(CH$_2$)$_{12}$CH$_3$ | 10 | 1a | 2a | 3h | 4h | 5h | 6h | | H | 8 |
| H | H | 10 | —CH$_2$(CH$_2$)$_{10}$CH$_3$ | H | 10 | 1a | 2i | 3i | 4i | 5i | | | I | 9 |
| H | OH | 10 | —OCH$_2$(CH$_2$)$_{12}$CH$_3$ | H | 10 | 1a | 2a | 3j | 4j | 5j | 6j | | J | 10 |
| OH | OH | 10 | —OCO(CH$_2$)$_{12}$CH$_3$ | H | 10 | | | | | | | 7k | K | 11 |
| OH | OH | 10 | —CH$_2$(CH$_2$)$_{12}$CH$_3$ | H | 10 | | | | | | | 7l | L | 12 |
| OH | OH | 10 | H | —OCO(CH$_2$)$_{12}$CH$_3$ | 10 | | | | | | | 7m | M | 13 |

TABLE 6-continued

| R$_1$ | R$_2$ | R$_3$ | R$_5$ R$_4$ | m | COMPOUND NUMBER 1 | 2 | 3 | 4 | 5 | 6 | 7 | (I) | Example |
|---|---|---|---|---|---|---|---|---|---|---|---|---|---|
| OH | OH | 10 H | —CH$_2$(CH$_2$)$_9$CH$_3$ | 13 | | | | | | | 7n | N | 14 |

EXAMPLE 1

1,5-Anhydro-2-deoxy-4,6-O-hydroxyphosphoryl-2-{(3R)-3-hydroxytetradecanamido}-3-O-{(2R)-2-tetradecanoyloxytetradecanoyl}-D-glucitol; (Compound A)

The First Step 1,5-Anhydro-2-deoxy-4,6-O-isopropyriden-2-[(3R)-3-{2-(trimethylsilyl)ethoxymethoxy}tetradecanamido]-D-glucitol; (Compound 2a)

2-Amino-1,5-anhydro-2-deoxy-4,6-O-isopropyriden-D-glucitol(1a) (5.8 g), (R)-3-{2-(trimethylsilyl)ethoxymethoxy}tetradecanoic acid (10.7 g), and WSC·HCl (11 g) were dissolved in dichloromethane (44 ml), and the resultant solution was stirred under ice-cooling for reaction. The reaction was monitored utilizing silica gel thin layer chromatography (chloroform:methanol=20:1). After the reaction went to completion, the mixture was diluted with dichloromethane, washed with water, and dried with anhydrous magnesium sulfate. The obtained solution was evaporated to remove the solvent, and the resultant residue was purified by silica gel column chromatography (chloroform:methanol=100:1). A colourless crystal compound (2a) (14 g, yield: 88%) was obtained.

[α]D: −6.90° (c=1.10, CH$_2$Cl$_2$).

m. p.: 61.0°–62.0° C.

IR(nujol)cm$^{-1}$: 3450, 3280, 1640, 1550, 1460, 1380, 860–835.

$^1$H-NMR(300 MHz)δTMS CDCl$_3$: 0.03(9H, s, Me$_3$Si), 0.85–0.97(5H, m, CH$_2$TMS, —Me), 1.20–1.60(20H, m, —CH$_2$—), 1.43, 1.52(6H, each s, —CMe$_2$), 2,38, 2,48(2H, AB part of ABX, J$_{AB}$=14,9 Hz, J$_{AX}$=6.6 Hz, J$_{BX}$=4.0 Hz, —CH$_2$CO—), 3.22(2H, m, H-1, H-5), 3.44(1H, brs, —OH), 3.54–3.65(4H, m, H-1, H-4, —CH$_2$CH$_2$TMS), 3.72(1H, t, J=10.5 Hz, H-6), 3.87–3.92(2H, m, H-6, CH—OSEM), 4.01–4.09(2H, m, H-2, H-3), 4.67, 4.75(2H, AB, J$_{AB}$=6.6 Hz, —OCH2O—), 6.47(1H, d, J=7.0Hz, NH).

The Second Step 1,5-Anhydro-2-deoxy-4,6-O-isopropyriden-3-O-{(2R)-2-tetradecanoyloxytetradecanoyl}-2-[(3R)-3-{2-(trimethylsilyl)ethoxymethoxy}tetradecanamido]-D-glucitol; (Compound 3a)

The compound 2a (1.73 g), (R)-2-tetradecanoyloxytetradecanoic acid (1.4 g), WSC·HCl (1.19 g), and DMAP (189 mg) were dissolved in dichloromethane (14.7 ml), and the obtained solution was stirred for three hours for reaction. The reacted solution was diluted with dichloromethane, washed with water, dried with anhydrous magnesium sulfate, and concentrated under reduced pressure. The obtained residue was purified by silica gel column chromatography (n-hexane:ethyl acetate=3:1) to obtain an amorphous compound (3a) (2.53 g, yield: 82.2%).

[α]D: +9.3° (c=1.1, CHCl$_3$).

IR(film)cm$^{-1}$: 3386, 2928, 2858, 1746, 1657, 1543, 1466, 1379.

$^1$H-NMR(300 MHz)δTMS CDCl$_3$: 0.02(9H, s, Me$_3$Si), 0.79–0.96(11H, m, —Me, CH$_2$TMS), 1.12–1.83(64H, m, —CH$_2$—), 1.35, 1.45(6H, each s, >CMe$_2$), 2.18–2.47(4H, m, —COCH$_2$—), 3.09–3.29(2H, m, H-1, H-5), 3.48–3.98(6H, m, H-1, H-4, H$_2$-6, —CH$_2$CH$_2$TMS), 4.04–4.26(2H, m, H-2, CHOSEM), 4.62–4.68(2H, AB, J$_{AB}$=6.8 Hz, —OCH2O—), 4.86(1H, t, J=6.3 Hz, >CHOCO—), 4.93(1H, t, H-3), 5.99(1H, d, J=7.3 Hz, NH).

The Third Step 1,5-Anhydro-2-deoxy-3-O-{(2R)-2-tetradecanoyloxytetradecanoyl}-2-[(3R)-3-{2-(trimethylsilyl)ethoxymethoxy}tetradecanamido]-D-glucitol; (Compound 4a)

The compound 3a (2.5 g) was dissolved in 95% acetic acid solution (32 ml), and the obtained solution was stirred in a water bath at 50° C. for five hours for reaction. The reacted solution was then diluted with toluene and concentrated under reduced pressure. The obtained residue was purified by silica gel column chromatography (chloroform:methanol=100:1) to obtain an amorphous compound (4a) (1.6 g, yield: 67.7%).

[α]D: +12.6° (c=1.65, CHCl$_3$).

IR(film)cm$^{-1}$: 3550–3150, 2926, 2858, 1742, 1655, 1543, 1460, 1365.

$^1$H-NMR(300 MHz)δTMS CDCl$_3$: 0.02(9H, s, Me$_3$Si), 0.80–0.99(11H, —Me, CH$_2$TMS), 1.17–1.89(64H, m, —CH$_2$—), 2.20–2.44(4H, m, —COCH$_2$—), 2.85(1H, brs, —OH), 3.14(1H, t, J=12.3 Hz, H-1), 3.25–3.37(1H, m, H-5), 3.48–3.68(3H, m, H-4, CH$_2$CH$_2$TMS), 3.70–3.81(1H, m, H-6), 3.82–3.96(2H, m, H-1, H-6), 4.01–4.20(2H, m, H-2, CHOSEM), 4.64–4.70(2H, AB, J$_{AB}$=6.9 Hz, —OCH2O—), 4.82(1H, t, J=6.5 Hz, >CHOCO—), 4.89(1H, t, J=10.1 Hz, H-3), 6.13(1H, d, J=7,4 Hz, NH).

The Fourth Step 1,5-Anhydro-2-deoxy-4,6-O-phenoxyphosphoryl-3-O-{(2R)-2-tetradecanoyloxytetradecanoyl}-2-[(3R)-3-{2-(trimethylsilyl)ethoxymethoxy} tetradecanamido]-D-glucitol; (Compound 5a)

The compound 4a (1.6 g) was dissolved in pyridine (1.6 ml) and dichloromethane (3.3 ml). To the resultant solution, phenyl dichlorophosphate (0.41 ml) was dropwise added under ice-cooling, followed by stirring for reaction. After four hours, the reacted solution was diluted with chloroform, washed with water, dried with anhydrous magnesium sulfate, and evaporated under reduced pressure to remove the solvent. The resultant residue was purified by silica gel column chromatography (chloroform) to obtain an amorphous compound 5a (437 mg, yield: 23.2%).

IR(film)cm$^{-1}$: 3306, 2926, 2858, 1744, 1655, 1595, 1460, 1379 1207, 944, 690.

$^1$H-NMR(300 MHz)δTMS CDCl$_3$: 0.01, 0.02(9H, each s, SiMe$_3$), 0.80–1.00(11H, m, —Me, —CH$_2$TMS), 1.14–1.69(64H, m, —CH$_2$—), 2.20–2.50(4H, m, —COCH$_2$—), 3.18–3.32(1H, m, H-1), 3.49–3.79(3H, m, H-5, —CH$_2$CH$_2$TMS), 3.88–4.00(1H, m, >CH—O-SEM), 4.06–4.56(5H, m, H-1, H-2, H-4, H$_2$-6), 4.63–4.70(2H, AB, J$_{AB}$=11.5 Hz, —OCH2O—), 4.72–4.88(1H, m, >CHOCO—), 5.12, 5.16(1H, each t, J=9.6 Hz, J=7.1 Hz, H-3), 6.00, 6.03(1H, each d, J=6.9 Hz, J=7.1 Hz, NH), 7.11–7.44(5H, m, Ph)

The Fifth Step 1,5-Anhydro-2-deoxy-2-{(3R)-3-hydroxytetradecanamido}-4,6-O-phenoxyphosphoryl-3-O-{(2R)-2-tetradecanoyloxytetradecanoyl}-D-glucitol; (Compound 6a)

The compound 5a (437 mg) was dissolved in dried dichloromethane (8.7 ml). To the solution, boron trifluoride etherate (0.44 ml) was dropwise added under ice-cooling, followed by stirring for thirty minutes for reaction. The reacted solution was diluted with dichloromethane, and washed with water, aqueous sodium bicarbonate solution, and water in this order. The obtained solution wa then dried with anhydrous magnesium sulfate, and evaporated under reduced pressure to remove the solvent. The obtained residual was purified by silica gel column chromatography (chloroform:methanol=100:1) to afford an amorphous compound (6a) (249 mg, yield: 64.7%).

IR(film)cm$^{-1}$: 3320, 2924, 2858, 1742, 1657, 1524, 1207.

$^1$H-NMR(300 MHz)δTMS CDCl$_3$: 0.88(9H, t, J=6.3 Hz, Me) 1.13–1.76(64H, m, —CH$_2$—), 2.21–2.49(4H, m, —COCH$_2$—), 3.21–3.42(2H, H-1, OH), 3.53–3.63, 3.69–3.80(1H, each m, H-5), 3.85–3.96(1H, m, >CH—OH), 4.01–4.56(5H, m, H-1, H-2, H-4, H$_2$-6), 4.70–4.85(1H, m, >CHOCO—), 5.19–5.32(1H, m, H-3), 6.50, 6.60(1H, each d, J=8.5 Hz, J=7.9 Hz, NH), 7.11–7.43(5H, m, Ph)

The Sixth Step

The compound 6a (50 mg) was dissolved in acetic acid (5 ml). To the solution was added platinum dioxide (20 mg), and this was stirred in an H$_2$ atmosphere under pressure (1.5 kg/cm$^2$) for two hours for reaction. The reacted solution was then filtered to remove the catalyst, and the filtrate was concentrated under reduced pressure. The obtained residue was suspended in 1,4-dioxane, and the obtained suspension was lyophilized to obtain a white powder compound (A) (45 mg, yield: 97.7%).

$^1$H-NMR: Hydrogen signals on the benzene ring completely disappeared.

m. p.: 103.6°–104.5° C. (decomp.).

IR(nujol)cm$^{-1}$: 3350, 1738, 1657, 1540. SI-MS: 887(m-H)$^-$.

EXAMPLE 2

1,5-Anhydro-2-deoxy-3-O-{(2RS)-2-dodecanoyloxyhexadecanoyl}-2-{(3R)-3-hydroxydodecanamido}-4,6-O-hydroxyphosphoryl-D-glucitol; (Compound B)

The First step 1,5-Anhydro-2-deoxy-4,6-O-isopropyriden-2-[(3R)-3-{2-(trimethylsilyl)ethoxymethoxy}dodecanamido]-D-glucitol; (Compound 2b)

Compound 2b was formed (1.7 g, yield: 57.3%) in the same manner as that for compound 2a, except that (R)-3-{2-(trimethylsilyl) ethoxymethoxy}dodecanoic acid (2.1 g) was used.

[α]D: −5.17° (c=0.97, CHCl$_3$).

m. p.: 91°–94° C.

IR(KBr)cm$^{-1}$: 3488, 2860, 1466, 1251, 1203, 1104.

$^1$H-NMR: the same as that for the compound 2a except for a —CH$_2$— integration value.

The Second Step 1,5-Anhydro-2-deoxy-3-O-{(2RS-2-dodecanoyloxyhexadecanoyl}-4,6-O-isopropyriden-2-[(3R)-3-{2-(trimethylsilyl)ethoxymethoxy}dodecanamido]-D-glucitol; (Compound 3b)

Compound 3b was formed (1.6 g, yield: 89.0%) in the same manner as that for compound 3a, except that compound 2b (1.0 .g) and (RS)-2-dodecanoyloxyhexadecanoic acid (800 mg) were used.

IR: the same as that for compound 3a $^1$H-NMR(300 MHz)δTMS CDCl$_3$: 0.02(9H, s, —SiMe$_3$), 0.86–0.94(11H, m, —Me, —CH$_2$TMS), 1.19–1.35(60H, m, —CH$_2$—), 1.35, 1.37, 1.45, 1.47(6H, each s, >CMe$_2$), 2.23–2.46(4H, m, —COCH$_2$—), 3.11–3.29(2H, m, H-1, H-5), 3.52–3.99(6H, m, H-2, H-4, H$_2$-6, —OCH$_2$CH$_2$TMS), 4.06–4.23(2H, m, H-2, >CHOCO), 4.95(1H, t, H-3), 6.01–6.05(1H, m, NH).

The Third Step 1,5-Anhydro-2-deoxy-3-O-{(2RS)-2-dodecanoyloxyhexadecanoyl}-2-[(3R)-3-{2-(trimethylsilyl)ethoxymethoxy}dodecanamido]-D-glucitol; (Compound 4b)

Compound 4b was obtained (1.0 g, yield: 52.8%) in the same manner as that for the compound 4a, except that compound 3b (2.0 g) was used.

IR: the same as that for the compound 3a.

$^1$H-NMR(300 MHz)δTMS CDCl$_3$: 0.02(9H, s, —SiMe$_3$), 0.80–0.98(11H, m, —Me, —CH$_2$TMS), 1.10–1.92(60H, m, —CH$_2$—), 2.23–2.45(4H, m, —COCH$_2$—), 3.15(1H, t, J=9.8 Hz, H-1), 3.31–3.38(1H, m, H-5), 3.53–3.83(4H, m, H-4, H-6, OCH$_2$CH$_2$TMS), 3.83–3.95(2H, m, H-1, H-6), 4.07–4.20(2H, m, H-2, >CHOSEM), 4.64–4.73(2H, m, —OCH2O—), 4.73–4.97(2H, m, H-3, >CHOCO—), 6.16–6.20(1H, m, NH).

The Fourth Step 1,5-Anhydro-2-deoxy-3-O-{(2RS)-2-dodecanoyloxyhexadecanoyl}-4,6-O-phenoxyphosphoryl-2-[(3R)-3-{2-(trimethylsilyl)ethoxymethoxy}dodecanamido]-D-glucitol; (Compound 5b)

Compound 5b was obtained (820 mg, yield: 71.4%) in the same manner as that for compound 5a, except that compound 4b (1.0 g) was used.

IR: the same as that for the compound 5a.

$^1$H-NMR(300 MHz)δTMS CDCl$_3$: 0.02(9H, s, —SiMe$_3$), 0.84–0.98(11H, m, —Me, —CH$_2$TMS), 1.17–1.77(60H, m, —CH$_2$—), 2.23–2.50(4H, m, —COCH$_2$—), 3.20–3.32(1H, m, H-1), 3.52–3.78(3H, m, H-5, —OCH$_2$CH$_2$TMS), 3.87–3.98(1H, m, >CHOSEM), 4.08–4.60(5H, m, H-1, H-2, H-4, H$_2$-6), 4.61–4.72(2H, m, —OCH2O—), 4.72–4.99(1H, m, >CHOCO), 5.09–5.23(1H, m, H-3), 6.08–6.41(1H, m, NH), 7.15–7.40(5H, m, Ph).

The fifth step 1,5-Anhydro-2-deoxy-3-O-{(2RS)-2-dodecanoyloxyhexadecanoyl}-2-{(3R)-3-hydroxydodecanamido}-4,6-O-phenoxyphosphoryl-D-glucitol; (Compound 6b)

Compound 6b was obtained (690 mg, yield: 94.7%) in the same manner as that for compound 6a, except that compound 5b (830 mg) was used.

IR: the same as that for the compound 5a.

$^1$H-NMR(300 MHz)δTMS CDCl$_3$: 0.89(9H, each t, J=6.9 Hz, Me), 1.23–1.96(60H, m, —CH$_2$—), 2.20–2.46(4H, m, —COCH$_2$—), 3.32–3.43(1H, m, H-1), 3.57–4.57(7H, m, H-1, H-2, H-4, H-5, H$_2$-6, >CHOH), 4.73–4.90(1H, m, >CHOCO), 5.21–5.33(1H, m, H-3), 6.29–6.64(1H, m, NH), 7.14–7.42(5H, m, Ph).

The sixth step

Compound B was obtained (80 mg, yield: 57.8%) in the same manner as that for compound A, except that compound 6b (150 mg) was used.

$^1$H-NMR: Hydrogen signal on the benzene ring completely disappeared.
m. p.: 122°–126° C. (decomp.)
IR(film)cm$^{-1}$: 3586, 2928, 1738, 1649, 1261.

EXAMPLE 3

1,5-Anhydro-2-deoxy-3-O-{(2RS)-2-hexadecanoyloxydodecanoyl}-2-{(3RS)-3-hydroxyhexadecanamido}-4,6-O-hydroxyphosphoryl-D-glucitol; (Compound C)

The first step 1,5,-Anhydro-2-deoxy-4,6-O-isopropyriden-2-[(3RS)-3-{2-(trimethylsilyl)ethoxymethoxy} hexadecanamido]-D-glucitol; (Compound 2c)

Compound 2c was obtained (2.6 g, yield: 81.7%) in the same manner as that for compound 2a, except that (RS)-3-{2-(trimethylsilyl)ethoxymethoxy}hexadecanoic acid (2.5 g) was used.

$^1$R(film)cm$^{-1}$: 3612, 1926, 1460, 1251, 1199, 1102.

$^1$H-NMR(300 MHz)δTMS CDCl$_3$: 0.03(9H, s, —SiMe$_3$), 0.85–0.98(5H, m, —CH$_2$TMS, —Me), 1.22–1.33(24H, m, —CH$_2$—), 1.44, 1.52(6H, each s, >CMe$_2$), 2.31–2.56(2H, m, —CH$_2$CO—), 3.16–3.25(2H, m, H-1, H-5), 3.54–3.65(4H, m, H-1, H-4, —OCH$_2$CH$_2$TMS), 3.72(1H, t, J=10.5 Hz, H-6), 3.86–3.94(2H, m, H-6, >CHOSEM), 3.98–4.13(2H, m, H-2, H-3), 4.66–4.77(2H, m, —OCH$_2$O—), 6.28–6.34(1H, m, NH).

The second step 1,5-Anhydro-2-deoxy-3-O-{(2RS)-2-hexadecanoyloxydodecanoyl}-4,6-O-isopropyriden-2-[(3RS)-3-{2-(trimethylsilyl}ethoxymethoxy)hexadecanamido]-D-glucitol; (Compound 3c) Compound 3c was formed (2.8 g, yield: 81.6%) in the same manner as that for compound 3a, except that compound 2c (2.0 g) and (RS)-2-hexadecanoyloxydodecanoic acid (1.5 g) were used.

IR: the same as that for compound 3a.

$^1$H-NMR(300 MHz)δTMS CDCl$_3$: 0.03(9H, s, —SiMe$_3$), 0.87–0.93(11H, m, —Me, —CH$_2$TMS), 1.15–1.35(68H, —CH$_2$—), 1.35, 1.36, 1.45, 1,47(6H, each s, >CMe$_2$), 2.28–2.61(4H, m, —COCH$_2$O—), 3.15–3.30(2H, m, H-1, H-5), 3.48–3.95(6H, m, H-1, H-4, H$_2$-6, —OCH$_2$CH$_2$TMS), 4.07–4.29(2H, m, H-2, >CHOSEM), 4.63–4.80(2H, m, —OCH$_2$O—), 4.86–5.02(2H, >CHOCO, H-3), 6.00–6.57(1H, m, NH).

The third step 1,5-Anhydro-2-deoxy-3-O-{(2RS)-2-hexadecanoyloxydodecanoyl}-2-[(3RS)-3-{2-(trimethylsilyl)ethoxymethoxy}hexadecanamido]-D-glucitol; (Compound 4c)

Compound 4c was obtained (1.7 g, yield: 70.2%) in the same manner as that for compound 4a, except that compound 3c (2.5 g) was used.

IR: the same as that for compound 4a.

$^1$H-NMR(300 MHz)δTMS CDCl$_3$: 0.02(9H, s, —SiMe$_3$), 0.85–0.98(11H, m, —Me, —CH$_2$TMS), 1.19–1.90(68H, m, —CH$_2$—), 2.22–2.47(4H, m, —COCH$_2$—), 3.10–3.26(1H, m, H-1), 3.26–3.39(1H, m, H-5), 3.50–3.94(6H, m, H-1, H-4, H$_2$-6, —OCH$_2$CH$_2$TMS), 4.08–4.20(2H, m, H-2, >CHOSEM), 4.64–4.97(4H, m, H-3, —OCH$_2$O—, >CHOCO—), 6.15–6.48(1H, m, NH).

The fourth step 1,5-Anhydro-2-deoxy-3-O-{(2RS)-2-hexadecanoyloxydodecanoyl}-4,6-O-phenoxyphosphoryl-2-[(3RS)-3-{2-(trimethylsilyl)ethoxymethoxy}-hexadecanamido-D-glucitol; (Compound 5c)

Compound 5c was obtained (1.3 g, yield: 68.0%) in the same manner as that for compound 5a, except that compound 4c (1.7 g) was used IR: the same as that for compound 5a.

$^1$H-NMR(300 MHz)δTMS CDCl$_3$: 0.03(9H, s, —SiMe$_3$), 0.87–0.99(11H, m, —Me, —CH$_2$TMS), 1.19–1.88(68H, m, —CH$_2$—), 2.27–2.68(4H, m, —COCH$_2$—), 3.20–3.37(1H, m, H-1), 3.51–3.82(3H, m, H-5, —OCH$_2$CH$_2$TMS), 3.82–3.99(1H, m, >CHOSEM), 4.11–4.60(5H, m, H-1, H-2, H-4, H$_2$-6), 4.60–5.00(3H, m, —OCH$_2$O—, >CHOCO—), 5.09–5.25(1H, m, H-3), 6.05–6.65(1H, m, NH), 7.16–7.41(5H, m, Ph).

The fifth step 1,5-Anhydro-2-deoxy-3-O-{(2RS)-2hexadecanoyloxydodecanoyl}-2-{(3RS)-3-hydroxyhexadecanamido}-4,6-O-phenoxyphosphoryl-D-glucitol; (Compound 6c)

Compound 6c was obtained (1.2 g, yield: 99.1%) in the same manner as that for compound 6a, except that compound 5c (1.4 g) was used.

IR: the same as that for compound 6a.

$^1$H-NMR(300 MHz)δTMS CDCl$_3$: 0.88(9H, each t, J=6.3 Hz, —Me$_3$), 1.19–1.92(68H, m, —CH$_2$—), 2.20–2.46(4H, m, —COCH$_2$—), 3.22–3.41(1H, m, H-1), 3.53–4.56(7H, m, H-1, H-2, H-4, H-5, H$_2$-6, >CHOH), 4.74–4.90(1H, m, >CHOCO), 5.18–5.31(1H, m, H-3), 6.22–6.83(1H, m, NH), 7.12–7.41(5H, m, Ph).

The sixth step

Compound C was obtained (140 mg, yield: 72.6%) in the same manner as that for compound A, except that compound 6c (210 mg) was used.

$^1$H-NMR: Hydrogen signals on the benzene ring completely disappeared.
m. p.: 124°–127° C. (decomp.).
IR(film)cm$^{-1}$: 3586, 2926, 2856, 1738, 1638, 1257.

EXAMPLE 4

1,5-Anhydro-2-deoxy-3-O-{(2RS)-2-dodecylhexadecanoyl}-4,6-O-hydroxyphosphoryl-2-{(3R)-3-hydroxytetradecanamido}-D-glucitol; (Compound D)

The second step 1,5-Anhydro-2-deoxy-3-O-{(2RS)-2-dodecylhexadecanoyl}-4,6-O-isopropyriden-2-[(3R)-3-{2-(trimethylsilyl)ethoxymethoxy}tetradecanamido ]-D-glucitol; (Compound 3d)

An amorphous compound 3d was prepared (2.5 g, yield: 90%) in the same manner as that for compound 3a, except that compound 2a (1.6 g) obtained in the first step of example 1 and (RS)-2-dodecylhexadecanoic acid (1.9 g) were used.

IR(film)cm$^{-1}$: 3480, 2900, 1720, 1655, 1530, 1460, 1370.

$^1$H-NMR(300 MHz)δTMS CDCl$_3$: 0.03(9H, s, Me$_3$Si), 0.83–0.94(11H, m, —CH$_2$TMS, —Me), 1.12–1.75(68H, m, —CH$_2$—), 1.32–1.43(6H, each s, CMe$_2$), 2.15–2.40(3H, m, —COCH$_2$—, —COCH<), 3.02–3.98(8H, m, H$_2$-1, H-4, H-5, H$_2$-6, —OCH$_2$CH$_2$TMS), 4.15–4.22(2H, m, H-2, >CH—O—SEM), 4.65(2H, s, —O—CH$_2$—O—), 4.92(1H, t, J=9.6 Hz, H-3), 6.18(1H, d, J=7.1 Hz, NH).

The third step 1,5-Anhydro-2-deoxy-3-O-{(2RS)-2-dodecylhexadecanoyl}-2-[(3R)-3-{2-(trimethylsilyl)ethoxymethoxy}-tetradecanamido]-D-glucitol; (Compound 4d)

An amorphous compound 4d was formed (1.2 g, yield: 64.8%) in the same manner as that for compound 4a, except that compound 3d (1.9 g) was used.

IR(nujol)cm$^{-1}$: 3500–3300, 1740, 1640, 1545.

$^1$H-NMR(300 MHz)δTMS CDCl$_3$: 0.02(9H, s, Me$_3$Si), 0.80–1.00(11H, m, —CH$_2$TMS, —Me), 1.10–1.71(68H, m, —CH$_2$—), 2.12–2.50(3H, m, —COCH$_2$—, —COCH<), 3 13(1H, t, J=10.3 Hz, H-1), 3.26–3.37(1H, m, H-5), 3.51–3.99(6H, m, H-1, H-4, H$_2$-6, —CH$_2$—CH$_2$TMS), 4.01–4.20(2H, m, >CH—OSEM, H-2), 4.67(2H, s, —O—CH$_2$—O—), 4.84(1H, t, J=10.2 Hz, H-3), 6.22(1H, d, J=7.3 Hz, NH).

The fourth step 1,5-Anhydro-2-deoxy-3-O-{(2RS)-2-dodecylhexadecanoyl}-4,6-O-phenoxyphosphoryl-2-[(3R)-3-{2-(trimethylsilyl)ethoxymethoxy} tetradecanamido]-D-glucitol; (Compound 5d)

An amorphous compound 5d was obtained (893 mg, yield: 74.8%) in the same manner as that for compound 5, except that compound 4d (1.1 g) was used.

IR(film)cm$^{-1}$: 3318, 2924, 2856, 1742, 1657, 1595, 1468, 1379, 1205, 963, 690.

$^1$H-NMR(300 MHz)δTMS CDCl$_3$: 0.06(9H, s, —Me$_3$Si), 0.71–1.04(11H, —CH$_2$TMS, —Me), 1.14–1.66(68H, m, —CH$_2$—), 2.20–2.50(3H, m, —COCH$_2$—, —COCH<), 3.11–3.30(1H, m, H-1), 3.54–3.80(3H, m, H-5, —CH$_2$CH$_2$TMS), 3.89–4.00(1H, m, >CH—OSEM), 4.11–4.58(5H, m, H-1, H-2, H-4, H$_2$-6), 4.70(2H, s, —O—CH$_2$—O—), 5.10, 5.16(1H, each t, J=9.6 Hz, J=9.6 Hz, H-3), 6.26, 6.33(1H, each d, J=7.1 Hz, J=7.2 Hz, NH), 7.13–7.46(5H, m, Ph).

The fifth step 1,5-Anhydro-2-deoxy-3-O-{(2RS)-2-dodecylhexadecanoyl}-2-{(3R)-3-hydroxytetradecanamido}-4,6-O-phenoxyphosphoryl-D-glucitol; (Compound 6d)

An amorphous compound 6d was obtained (758 mg, yield: 96.7%) in the same manner as that for compound 6a, except that compound 5d (758 mg) was used.

IR(nujol)cm$^{-1}$: 3586–3366, 1736, 1640, 1539, 1164, 1048.

$^1$H-NMR(300 MHz)δTMS CDCl$_3$: 0.88(9H, t, J=6.2 Hz, —Me), 1.09–1.56(68H, m, —CH$_2$—), 2.10–2.50(3H, m, —COCH$_2$—, —COCH<), 3.06–3.29(2H, m, H-1, OH), 3.51–3.62, 3.67–3.79(1H, each m, H-5), 3.87–3.99(1H, m, >CH—OH), 4.07–4.56(5H, m, H-1, H-2, H-4, H$_2$-6), 5.06, 5.13(1H, each t, J=10.5 Hz, J=9.9 Hz, H-3), 6.20, 6.28(1H, each d, J=6.9 Hz, J=5.7 Hz, NH), 7.10–7.44(5H, m, Ph).

The sixth step

A white powder compound D was obtained (38 mg, yield: 83%) in the same manner as that for compound A with the exception that compound 6d (50 mg) was used.

$^1$H-NMR: Hydrogen signals on the benzene ring completely disappeared.

m. p.: 151.0°–152.0° C. (decomp.).
IR(film)cm$^{-1}$: 2924, 2856, 1736, 1649, 1543, 1247.

EXAMPLE 5

1,5-Anhydro-2-deoxy-3-O-{(2RS)-2-dodecyloctadecanoyl}-2-{(3R)-3-hydroxydodecanamido}-4,6-O-hydroxyphosphoryl-D-glucitol; Compound E)

The second step 1,5-Anhydro-2-deoxy-3-O-{(2RS)-2-dodecyloctadecanoyl}-4,6-O-isopropyriden-2-[(3R)-3-{2-(trimethylsilyl)ethoxymethoxy}dodecanamido]-D-glucitol; (Compound 3e)

A compound 3e was prepared (1.2 g, yield: 67.1%) in the same manner as that for compound 3a, except that compound 2b (1.0 g) obtained in the first step of example 2 and (RS)-2-dodecyloctadecanoic acid (853 mg) were used.

IR: the same as that for compound 3d.
$^1$H-NMR: the same as that for the compound 3d.

The third step 1,5-Anhydro-2-deoxy-3-O-{(2RS)-2-dodecyloctadecanoyl}-2-[(3R)-3-(2-(trimethylsilyl)ethoxymethoxy}dodecanamido]-D-glucitol; (Compound 4e)

Compound 4e was obtained (838 mg, yield: 71.7%) in the same manner as that for compound 4a with the exception that compound 3e (1.2 g) was used.

IR: the same as that for compound 4d.
$^1$H-NMR: the same as that for compound 4d.

The fourth step 1,5-Anhydro-2-deoxy-3-O-{(2RS)-2-dodecyloctadecanoyl}-4,6-O-phenoxyphosphoryl-2-[(3R)-3-{2-(trimethylsilyl)ethoxymethoxy}dodecanamido]-D-glucitol; (Compound 5e)

A compound 5e was obtained (177 mg, yield: 78.2%) in the same manner as that for compound 5a with the exception that compound 4e (200 mg) was used.

IR: the same as that for compound 5d.
$^1$H-NMR: the same as that for compound 5d.

The fifth step 1,5-Anhydro-2-deoxy-3-O-{(2RS)-2-dodecyloctadecanoyl}-2-{(3R)-3-hydroxydodecanamido}-4,6-O-phenoxyphosphoryl-D-glucitol; (Compound 6e)

Compound 6e was obtained (133 mg, yield: 85.8%) in the same manner as that for compound 6a, except that compound 5e (177 mg) was used.

IR: the same as that for compound 6d.
$^1$H-NMR: the same as that for compound 6d .

The sixth step

Compound E was formed (36 mg, yield: 78.5%) in the same manner as that for compound A, except that the compound 6e (50 mg) was used.

$^1$H-NMR: Hydrogen signal on the benzene ring completely disappeared m.p.: 154.5°–155.5° C. (decomp.).
IR: the same as that for compound D.

EXAMPLE 6

1,5-Anhydro-3-O-{(2RS)-2-decyloctadecanoyl}-2-deoxy-2-{(3RS)-3-hydroxyhexadecanamido}-4,6-O-hydroxyphosphoryl-D-glucitol; (Compound F)

The second step 1,5-Anhydro-3-O-{(2RS)-2-decyloctadecanoyl}-2-deoxy-4,6-O-isopropyriden-2-[(3RS)-3-{2-(trimethylsilyl)ethoxymethoxy}hexadecanamido]-D-glucitol; (Compound 3f)

A compound 3f was prepared (822 mg, yield: 48.6%) in the same manner as that for compound 3a, except that compound 2c (1.0 g) obtained in the first step of example 3 and (RS)-2-decyloctadecanoic acid (724 mg) were used.

IR: same as that for the compound 3d.

$^1$H-NMR: the same as that for compound 3d, except for the —$CH_2$— integration value.

The third step 1,5-Anhydro-3-O-{(2RS)-2-decyloctadecanoyl}-2-deoxy-4,6-O-phenoxyphosphoryl-2-[(3RS)-3-{2-(trimethylsilyl)ethoxymethoxy} hexadecanamido]-D-glucitol; (Compound 4f)

Compound 4f was obtained (565 mg, yield: 76.6%) in the same manner as that for compound 4a with the exception that compound 3f (822 mg) was used.

IR: the same as that for compound 4d.

$^1$H-NMR: the same as that for compound 4d except for the —$CH_2$— integration value.

The fourth step 1,5-Anhydro-3-O-{(2RS)-2-decyloctadecanoyl}-2-deoxy-2-[(3RS)-3-{2-(trimethylsilyl)ethoxymethoxy} hexadecanamido]-D-glucitol; (Compound 5f)

Compound 5f was obtained (184 mg, yield: 81.6%) in the same manner as that for compound 5a with the exception that compound 4f (200 mg) was used.

IR: the same as that for compound 5d.

$^1$H-NMR: the same as that for compound 5d except for the —$CH_2$— integration value.

The fifth step 1,5-Anhydro-3-O-{(2RS)-2-decyloctadecanoyl}-2-deoxy-2-{(3RS)-3-hydroxyhexadecanamido}-4,6-O-phenoxyphosphoryl-D-glucitol; (Compound 6f)

A compound 6f was obtained (145 mg, yield: 89.7%) in the same manner as that for compound 6a, except that compound 5f (184 mg) was used.

IR: the same as that for compound 6d.

$^1$H-NMR: the same as that for compound 6d except for the —$CH_2$— integration value.

The sixth step

A compound F was obtained (31 mg, yield: 60.0%) in the same manner as that for compound A, except that compound 6f (50 mg) was used.

$^1$H-NMR: Hydrogen signals on the benzene ring completely disappeared.

m. p.: 159.7°–161.4° C. (decomp.).

IR: the same as that for compound D.

EXAMPLE 7

1,5-Anhydro-2-deoxy-4,6-O-hydroxyphosphoryl-2-{(3R)-3-hydroxytetradecanamido}-3-O-{(3R)-3-tetradecanoyloxytetradecanoyl}-D-glucitol; (Compound G)

The second step 1,5-Anhydro-2-deoxy-4,6-O-isopropyriden-3-O-{(3R)-3-tetradecanoyloxytetradecanoyl}-2-[(3R)-3-{2-(trimethylsilyl)ethoxymethoxy}tetradecanamido]-D-glucitol; (Compound 3 g)

An amorphous compound 3 g was prepared (2.0 g, yield: 79.6%) in the same manner as that for compound 3a with the exception that compound 2a (1.38 g) obtained in the first step of example 1 and (R)-3-tetradecanoyloxytetradecanoic acid (1.12 g) were used.

[α]D: +0.05° (c=1.25, CHCl$_3$).

IR(film)cm$^{-1}$: 3316, 2926, 2858, 1738, 1647, 1543, 851, 835.

$^1$H-NMR(300 MHz)δTMS CDCl$_3$: 0.02(9H, s, SiMe$_3$), 0.78–0.98(11H, m, —Me, —CH$_2$TMS), 1.08–1.66(62H, m, —$CH_2$—), 1.33, 1.46(6H, each s, >CMe$_2$), 2.17–2.39(4H, m, —COCH$_2$—), 2.47–2.65(2H, AB part of ABX, $J_{AB}$=32.2 Hz, $J_{AX}$=7.2 Hz, $J_{BX}$=9.5 Hz, —NHCO$\underline{CH_2}$—), 3.10(1H, t, J=9.9 Hz, H-1), 3.16–3.28(1H, m, H-5), 3.49–3.94(6H, m, H-1, H-4, H$_2$-6, $\underline{CH_2}$CH$_2$TMS), 4.02–4.20(2H, m, H-2, >CHOSEM), 4.62–4.68(2H, AB, $J_{AB}$=13.1 Hz, —OCH$_2$O—), 4.89(1H, t, J=10.4 Hz, H-3), 5.09–5.20(1H, m, —COCH$_2$$\underline{CH}$CO), 6.22(1H, d, J=6.3 Hz, NH).

The third step 1,5-Anhydro-2-deoxy-3-O-{(3R)-3-tetradecanoyloxytetradecanoyl}-2-[(3R)-3-{2-(trimethylsilyl)ethoxymethoxy}tetradecanamido]-D-glucitol; (Compound 4g)

An amorphous compound 4g was obtained (1.6 g, yield: 84.2%) in the same manner as that for compound 4a with the exception that compound 3 g (2.0 g) was used.

[α]D: +5.55° (c=1.25, CHCl$_3$)

IR(film)cm$^{-1}$: 3580–3190, 2922, 2856, 1736, 1651, 1551, 861, 835.

$^1$H-NMR(300 MHz)δTMS CDCl$_3$: 0.02(9H, s, SiMe$_3$), 0.80–1.00(11H, m, —Me, —CH$_2$TMS), 1.12–1 71(62H, m, —$CH_2$—), 2.24–2.41(4H, m, —COCH$_2$—), 2.53(2H, d, J=5.4 Hz, —NH, —CO$\underline{CH_2}$—), 3.11(1H, t, J=10.8 Hz, H-1), 3.26–3.38(1H, m, H-5), 3.43–4.21(8H, m, H-1, H-2, H-4, H$_2$-6, —$\underline{CH_2}$CH$_2$TMS, >CHOSEM), 4.70–4.63(2H, AB, $J_{AB}$=14.5 Hz, —OCH$_2$O—), 4.81(1H, t, J=10.3 Hz, H-3), 5.05–5.17(1H, m, >CHCO—), 6.40(1H, d, J=7.0 Hz, NH).

The fourth step 1,5-Anhydro-2-deoxy-4,6-O-phenoxyphosphoryl-3-O-{(3R)-3-tetradecanoyloxytetradecanoyl}-2-[(3R)-3-{2-(trimethylsilyl)ethoxymethoxy}tetradecanamido]-D-glucitol; (Compound 5 g)

An amorphous compound 5 g (0.821 g, yield: 70.3%) was obtained in the same manner as that for compound 5a with the exception that compound 4g (1.02 g) was used.

IR(film)cm$^{-1}$: 3586, 2926, 1744, 1667, 1539, 1466, 1379.

$^1$H-NMR(300 MHz)δTMS CDCl$_3$: 0.02–0.11(9H, each s, —SiMe$_3$), 0.81–1.00(11, m, —Me, —CH$_2$TMS), 1.12–1.67(62H, m, —$CH_2$—), 2.20–2.66(6H, m, —COCH$_2$—), 3.08–3.28(1H, m, H-3), 3.50–3.79(3H, m, H-5, —$\underline{CH_2}$CH$_2$TMS), 3.81–3.97(1H, m. >CHOSEM), 4.05–4.55(5H, m, H-1, H-2, H-4, H$_2$-6), 4.61–4.79(2H, m, —OCH$_2$O—), 5.01–5.28(2H, m, H-3, >CHCO), 6.40–6.51(1H, m, NH), 7.24–7.45(5H, m, Ph).

The fifth step 1,5-Anhydro-2-deoxy-2-{(3R)-3-hydroxytetradecanamido}-4,6-O-phenoxyphosphoryl-3-O-{(3R)-

3-tetradecanoyloxytetradecanoyl}-D-glucitol; (Compound 6g)

An amorphous compound 6g (320 mg, yield: 44.2%) was obtained in the same manner as that for compound 6a with the exception that compound 5g (821 mg) was used.

IR(film)cm$^{-1}$: 3586 1742, 1651, 1543, 1168, 1052.

$^1$H-NMR(300 MHz)δTMS CDCl$_3$: 0.88(9H, t, J=5.0 Hz, Me), 1.18–1.70(62H, m, —CH$_2$—), 2.20–2.63(6H, m, —COCH$_2$—), 3.18–3.42(2H, m, H-1, OH), 3.51–3 62, 3.70–3.80(1H, each m, H-5), 3.83–3.96(1H, m, >CHOH), 4.02–4.57(5H, m, H-1, H-2, H-4, H$_2$-6), 5.04–5.21(2H, m, H-3, >CHOCO), 6.67, 6.77(1H, each d, J=6.8 Hz, J=4.9 Hz, NH), 7.14–7.43(5H, m, Ph).

The sixth step

A white powder of compound G was obtained (90 mg, yield: 97.7%) in the same manner as that for compound A, except that compound 6g (100 mg) was used:

$^1$H-NMR: Hydrogen signals on the benzene ring completely disappeared.

[α]D: −1.55° (c=1.1, CHCl$_3$: MeOH=1.1).

m. p.: 274.1°–277.9° C. (decomp.)

IR(film)cm$^{-1}$: 2858, 1719, 1651, 1462.

EXAMPLE 8

1,5-Anhydro-2-deoxy-4,6-O-hydroxyphosphoryl-2-{(3R)-3-hydroxytetradecanamido]-3-O-{(3RS)-3-undecylheptadecanoyl}-D-glucitol; (Compound H)

The second step 1,5-Anhydro-2-deoxy-4,6-O-isopropyriden-2-[(3R)-3-{2-(trimethylsilyl)ethoxymethoxy}tetradecanamido]-3-O-{(3RS)-3-undecylheptadecanoyl}-D-glucitol; (Compound 3h)

An amorphous compound 3h was prepared (4.12 g, yield: 91%) in the same manner as that for compound 3h, except that compound 2a (3.0 g) obtained in the first step of example 1 and (RS)-3-undecylheptadecanoic acid (2.0 g) were used.

IR(film)cm$^{-1}$: 3320, 2900, 1735, 1645, 1545, 1470, 1383.

$^1$H-NMR(300 MHz)δTMS CDCl$_3$: 0.03(9H, s, Me$_3$Si), 0.86–0.97(11H, m, —CH$_2$TMS, —Me), 1.18–1.60(66H, m, —CH$_2$—), 1.36, 1.47(6H, each s, CMe$_2$), 1.85(1H, m, —CH<), 2.20–2.40(4H, m, —CH$_2$CO—), 3.10–4.00(8H, m, H$_2$-1, H-4, H-5, H$_2$-6, —O—CH$_2$CH$_2$TMS), 4.16(2H, m, H-2, —CH—OSEM), 4.66, 4.68(2H, AB, J$_{AB}$=6.9 Hz, —OCH$_2$O—), 4.94(1H, t, J=9.6 Hz, H-3), 6.27(1H, d, J=7.0 Hz, NH).

The third step 1,5-Anhydro-2-deoxy-2-[(3R)-3-{2-(trimethylsilyl)ethoxymethoxy}tetradecanmido]-3-O-{(3RS)-3-undecylheptadecanoyl}-D-glucitol; (Compound 4h)

An amorphous compound 4h was formed (1.84g, yield: 91%) in the same manner as that for compound 4a with the exception that compound 3h (2.79 g) was used.

IR(film)cm $^{-1}$: 3600–3100, 2900, 1720, 1650, 1540, 1463, 1380.

$^1$H-NMR(300 MHz)δTMS CDCl$_3$: 0.02(9H, s, —SiMe$_3$), 0.85–0.96(11H, m, —CH$_2$TMS, —Me), 1.10–1.65(66H, m, —CH$_2$—), 1.85(1H, m, —CH<), 2.20–2.40(4H, m, —COCH$_2$—), 2.65(1H, brs, —OH), 3.13(1H, t, J=10.0 Hz, H-1), 3.32(1H, m, H-5), 3.52–3.95(6H, m, H-1, —CH$_2$—CH$_2$TMS, H-4, H$_2$-6), 4.0–4.17(2H, m, H-2, —CH—OSEM), 4.63, 4.69(2H, AB, J=7.0 Hz, —OCH$_2$O—), 4.85(1H, t, J=9.4 Hz, H-3), 6.29(1H, d, J=7.3 Hz, NH).

The fourth step 1,5-Anhydro-2-deoxy-4,6-O-phenoxyphosphoryl-2-(3R)-3-{2-(trimethylsilyl)ethoxymethoxy}tetradecanamido]-3-O-{(3RS)-3-undecylheptadecanoyl}-D-glucitol; (Compound 5h)

An amorphous compound 5h was obtained (1.0 g, yield: 80.5%) in the same manner as that for compound 5a with the exception that compound 4h (1.1 g) was used.

IR(film)cm$^{-1}$: 3308, 2926, 1744, 1659, 1595, 1466, 1707, 1379, 944, 665.

$^1$H-NMR(300 MHz)δTMS CDCl$_3$: 0.02(9H, s, —SiMe$_3$), 0.80–0.99(11H, m, —Me, —CH$_2$TMS), 1.11–1.60(66H, m, —CH$_2$—), 1.69–1.90(1H, m, >CH—), 2.14–2.41(4H, m, —COCH$_2$—), 3.08–3.27(1H, m, H-1), 3.50–3.77(3H, m, H-5, —CH$_2$CH$_2$TMS), 3.81–3.92(1H, m, >CHOSEM), 4.04–4.54(5H, m, H-1, H-2, H-4, H$_2$-6), 4.61–4.72(2H, m, —OCH$_2$O—), 5.02–5.18(1H, m, H-3), 6.29, 6.36(1H, each d, J=7.5 Hz, J=4.9 Hz, NH), 7.10–7.40(5H, m, Ph).

The fifth step 1,5-Anhydro-2-deoxy-2-{(3R)-3-hydroxytetradecanamido}-4,6-O-phenoxyphosphoryl-3-O-{(3RS)-3-undecylheptadecanoyl}-D-glucitol; (Compound 6h)

A compound 6h was obtained (751 mg, yield: 86.0%) in the same manner as that for compound 6a with the exception that compound 5h (1.0 g) was used.

IR(film)cm$^{-1}$: 3586, 3296, 1742, 1651, 1543, 1168, 1052.

$^1$H-NMR(300 MHz)δTMS CDCl$_3$: 0.88(9H, t, J=6.4 Hz, —Me), 1.14–1.52(66H, m, —CH$_2$—), 1.70–1.90(1H, m, >CH—), 2.14–2.45(4H, m, —COCH$_2$), 3.13–3.31(1H, m, H-1), 3.52–3.64, 3.69–3.79(1H, each m, H-5), 3.85–3.99(1H, m, >CHOH), 4.08–4.57(5H, m, H-1, H-2, H-4, H$_2$-6), 5.10–5 29(1H, m, H-3), 6.27, 6.39(1H, each d, J=7.1 Hz, J=7.3 Hz, NH), 7.11–7.42(5H, m, Ph).

The sixth step

A white power H was formed (38 mg, yield 82.7%) in the same manner as that for compound A with the exception that compound 6h (100 mg) was used.

$^1$H-NMR: Hydrogen signals on the benzene ring completely disappeared.

m. p.: 153.2°–156.3° C. (decomp.).

IR(film)cm$^{-1}$: 2922, 1649, 1543, 1460.

EXAMPLE 9

1,5-Anhydro-2-deoxy-3-O-(2-dodecyltetradecanoyl)-4,6-O-hydroxyphosphoryl-2-tetradecanamido-D-glucitol; (Compound I)

The first step 1,5-Anhydro-2-deoxy-4,6-O-isopropyriden-2-tetradecanamido-D-glucitol; (Compound 2i)

A compound 2i was formed in the same manner as that for compound 2a with the exception that tetradecanoic acid (2.3 g) was used.

[α]D: −9.4° (c=1.01, CHCl$_3$).

m. p.: 108.0°–109.0° C.

IR(film)cm$^{-1}$: 3308, 2922, 2854, 1647, 1547, 1468.

$^1$H-NMR(300 MHz)δTMS CDCl$_3$: 0.88(9H, t, J=6.7 Hz, Me), 1.16–1.38(20H, m, —CH$_2$—), 1.43, 1.52(6H, each s, >CMe₂), 1.57-1.69(2H, m, —COCH₂CH₂—), 2.14-2.28(2H, m, —COCH₂—), 3.18(1H, t, J=10.8 Hz, H-1), 3.11-3.22(1H, m, H-5), 3.47-3.63(2H, m, H-1, H-4), 3.72(1H, t, J=10.6 Hz, H-6), 3.90(1H, dd, J=5.4 Hz, J=10.8 Hz, H-6), 3.94-4.08(1H, m, H-2), 4.15(1H, dd, J=5.4 Hz, J=10.9 Hz, H-3), 5.54(1H, d, J=6.6 Hz, NH).

The second step 1,5-Anhydro-2-deoxy-3-O-(2-dodecyltetradecanoyl)-4,6-O-isopropyriden-2-tetradecanamido-D-glucitol; (Compound 3i)

A compound 3i was obtained (1.3 g, yield: 84.0%) in the same manner as that for compound 3a with the exception that the compound 2i (833 mg and 2-tetradecyldecanoic acid (776 mg) were used.

[α]D: −8.5° (c=1.27, CHCl₃).
m. p.: 52.8°-54.0° C.
IR(film)cm⁻¹: 3298, 2922, 2854, 1734, 1649, 1545, 1468
¹H-NMR(300 MHz)δTMS CDCl₃: 0.88(9H, t, J=6.7 Hz, Me), 1.10-1.65(66H, m, —CH₂—), 1.35, 1.47(6H, each s, >CMe₂), 2.09(2H, t, J=7.7 Hz, —COCH₂—), 2.26-2.42(1H, m, COCH<), 3.12(1H, t, J=10.0 Hz, H-1), 3.20-3.32(1H, m, H-5), 3.65-3.79(2H, m, H-1, H-6), 3.92 - (1H, dd, J=5.2 Hz, J=10.7 Hz, H-6), 4.06-4.27(2H, m, H-4, H-2), 4.92(1H, t, H=9.7 Hz, H-3), 5.89(1H, d, J=6.9 Hz, NH).

The third step 1,5-Anhydro-2-deoxy-3-O-(2-dodecyltetradecanoyl)-2-tetradecanamido-D-glucitol; (Compound 4i)

A compound 4i was obtained (1.1 g, yield: 84.0%) in the same manner as that for compound 4a with the exception that compound 3i (1.2 g) was used.

[α]D: −0.089° (c=1.05, CHCl₃).
m. p.: 99.0° C.
IR(film)cm⁻¹: 3372, 3320, 2922, 2856, 1736, 1647, 1537, 1466.
¹H-NMR(300 MHz)δTMS CDCl₃: 0.88(9H, t, J=6.9 Hz, Me), 1.08-1.67(66H, m, —CH₂—), 2.09(2H, t, J=7.8 Hz, —COCH₂—), 2.27-2.46(1H, m, —COCH<), 3.13(1H, t, J=10.5 Hz, H-1), 3.23-3.34(1H, m, H-5), 3.68-3.96(3H, m, H-1, H₂-6), 3.98-4.19(2H, m, H-2, H-4), 4.89(1H, t, J=9.7 Hz, H-3), 6.07(1H, d, J=7.0 Hz, NH).

The fourth step 1,5-Anhydro-2-deoxy-3-O-(2-dodecyltetradecanoyl)-4,6-O-phenoxyphosphoryl-2-tetradecanamido-D-glucitol; (Compound 5i)

Compound 5i was obtained (969 mg, yield: 84.0%) om the same manner as that for compound 5a with the exception that compound 4i (969 mg) was
m. p.: 86.4°-87.0° C.
IR(film)cm⁻¹: 3380, 2918, 2854, 1738, 1669, 1595, 1493, 1468, 1379, 1301, 1207, 768.
¹H-NMR(300 MHz)δTMS CDCl₃: 0.88(9H, t, J=6.6 Hz, Me), 1.11-1.72(66H, m, —CH₂—), 2.90(2H, t, J=7.6 Hz, —COCH₂—), 2.26-2.49(1H, m, —COCH<), 3.13, 3.19(1H, each t, J=10.5 Hz, J=10.2 Hz, H-1), 3.52-3.63, 3.67-3.79(1H, each m, H-5), 4.04-4.53(5H, m, H-1, H-2, H-4, H₂-6), 5.03, 5.11(1H, each t, J=9.9 Hz, J=9.8 Hz, H-3), 5.86, 5.96(1H, each d, J=6.8 Hz, J=7.0 Hz, NH), 7.10-7.41(5H, m, Ph).

The sixth step

Compound I was formed (219 mg, yield: 41.0%) in the same manner as that for compound A, with the exception that compound (5i) (585 mg) was used.
[α]D: −0.39° (c=1.00, CHCl₃)
m. p.: 93.0°-96.0° C.
IR(film)cm⁻¹: 3296, 2924, 2856, 1736, 1651, 1543, 1468, 1379, 1257, 1178.

EXAMPLE 10

1,5-Anhydro-2-deoxy-4,6-O-hydroxyphosphoryl-2-{(3R)-3-hydroxytetradecanamido}-3-O-{(3RS)-3-tetradecyloxytetradecanoyl}-D-glucitol; (Compound J)

The second step 1,5-Anhydro-2-deoxy-4,6-O-isopropyriden-3-O-{(3RS)-3-tetradecyloxytetradecanoyl}-2-[(3R-3-{2-(trimethylsilyl)ethoxymethoxy}tetradecanamido]-D-glucitol; (Compound 3j)

An amorphous compound 3j was prepared (8.1 g, yield: 87.5%) in the same manner as that for compound 3a, with the exception that compound 2a (5.3 g) obtained in the first step of example 1 and (RS)-3-tetradecyloxytetradecanoic acid (4.1 g) were used.
IR(KBr)cm⁻¹: 3308, 2926, 2858, 1734, 1647, 1547, 1466, 1371, 1251, 1201, 1106, 1056.
¹H-NMR(300 MHz)δTMS CDCl₃: 0.02(9H, s, SiMe₃), 0.75-1.00(11H, m, Me, —CH₂TMS), 1.00-1.61(65H, m, —CH₂—, >CH—), 1.34, 1.46(each s, Me₂C<), 2.19-2.70(4H, m, —COCH₂—), 3.04-3.96(H₂-1, H-4, H-5, H₂-6, —CH₂CH₂TMS, —OCH₂CH₂—), 4.05-4.22(2H, m, H-2, >CHOSEM), 4.57-4.72(2H, m, —OCH₂O—), 4.86-5.00(1H, m, H-3), 6.26(1H, d, J=6.9 Hz, NH).

The third step 1,5-Anhydro-2-deoxy-3-O-{(3RS)-3-tetradecyloxytetradecanoyl}-2-[(3R)-3-{2-(trimethylsilyl)-ethoxymethoxy}tetradecanamido]-D-glucitol; (Compound 4J)

An amorphous compound 4j was obtained (6.1 g, yield: 78.5%) in the same manner as that for compound 4a, with the exception that compound 3j (8.0 g) was used.
IR(KBr)cm⁻¹: 3310, 2926, 2858, 1729, 1657, 1539, 1466, 1379, 1305, 1251, 1158, 1104.
¹H-NMR(300 MHz)δTMS CDCl₃: 0.02(9H, m, SiMe₃), 0.78-1.00(11H, m, Me, —CH₂TMS), 1.00-1.70(65H, m, —CH₂—, >CH—), 2.21-2.78(4H, m, —COCH₂—), 3.12(1H, J=10.5 Hz, H-1), 3.26-3.95(9H, m, H-1, H-4, H-5, H₂-6, —CH₂CH₂TMS, —OCH₂CH₂—), 4.00-4.21(2H, m, H-2, >CHOSEM), 4.65, 4.68(2H, AB, J_AB=6.8 Hz, —OCH₂O—), 4.71-4.90(1H, m, H-3), 6.27-6.60(1H, m, NH).

The fourth step 1,5-Anhydro-2-deoxy-4,6-O-phenoxyphosphoryl-3-O-{(3RS)-3-tetradecyloxytetradecanoyl}-2-[(3R)-3-{2-(trimethylsilyl)ethoxymethoxy} tetradecanamido]-D-glucitol; (Compound 5j)

An amorphous compound 5j was formed (878 g, yield: 77.6%) in the same manner as that for compound 5a, with the exception that compound 4j (1.0 g) was used.
IR(KBr)cm⁻¹: 2926, 2858, 1744, 1657, 1543, 1493, 1466, 1305, 1251, 1104, 1054.

¹H-NMR(300 MHz)δTMS CDCl₃: 0.02(9H, m, SiMe₃), 0.77-1.00(11H, m, Me, —CH₂TMS), 1.00-1.61(65H, m, —CH₂—, >CH—), 2.15-2.72(4H, m, —COCH₂—), 3.09-4.55(12H, m, H₂-1, H-2, H-4, H-5, H₂-6, —C$\underline{H_2}$CH₂TMS, —OC$\underline{H_2}$CH₂, >CHO-SEM), 4.55-4.72(2H, m, —OCH₂O—), 5.01-5.20(1H, m, H-3), 6.22-6.40(1H, m, NH), 7.10-7.40(5H, m, Ph).

The fifth step 1,5-Anhydro-2-deoxy-2-{(3R)-3-hydroxytetradecanamido}-4,6-O-phenoxyphosphoryl-3-O-(3RS)-3-tetradecyloxytetradecanoyl}-D-glucitol; (Compound 6j)

An amorphous compound 6j was obtained (710 g) in the same manner as that for compound 6a, with the exception that compound 5j (845 mg) was used.

IR(KBr)cm⁻¹: 3296, 2922, 2856, 1742, 1655, 1595, 1547, 1491, 1468, 1309, 1207, 1174.

¹H-NMR(300 MHz)δTMS CDCl₃: 0.88(9H, t, J=6.4 Hz, Me), 1.00-1.63(65H, m, —CH₂—, >CH—), 2.10-2.71(4H, m, —COCH₂—), 3.18-4.60(10H, m, H₂-1, H-2, H-4, H-5, H₂-6, >C$\underline{H}$OH, —OC$\underline{H_2}$CH₂—), 5.11-5.31(3H, m, H-3), 6.40-6.70(1H, m, NH), 7.11-7.45(5H, m, Ph).

The sixth step

A white powder of compound (J) was obtained (91 mg, yield: 93.4%) in the same manner as that for compound A, with the exception that compound 6j (100 mg) was used.

¹H-NMR: Hydrogen signals on the benzene ring completely disappeared.

m. p.: 161°-164° C.

IR(KBr)cm⁻¹: 1 3272, 2924, 2854, 1740, 1647, 1543, 1468, 1363, 1259, 1176.

EXAMPLE 11

2-deoxy-4,6-O-hydroxyphosphoryl-2-{(3R)-3-hydroxytetradecanamido}-3-O-{(2RS)-tetradecanoyloxytetradecanoyl}-D-glucopyranose; (Compound K)

The seventh step 30 mg of 2-deoxy-2-{(3R)-3-hydroxytetradecanamido}-4-O-phosphono-3-O-{(2RS)-2-tetradecanoyloxytetradecanoyl}-D-glucopyranose(7k) which can be produced in the manner disclosed in Japanese Patent Disclosure No. 62888/90 was dissolved in a mixture of tetrahydrofuran: chloroform (1:1) (10 ml). To the resultant solution, DCC (5 mg) was added, followed by stirring for three hours. The reacted solution was subjected to Sephadex column chromatography (LH-20, chloroform:methanol=1:1). Further, the solution was lyophilized by utilizing 1,4-dioxane to obtain compound K.

m. p.: 158°-160° C.

IR(KBr)cm⁻¹: 3300, 2950, 2860, 1740, 1680, 1590,
C₄₈H₈₉NO₁₂P (903.21). theoretical value: C=63.83%, H=9.93%, N=1.55%. actual value: C=64.04%, H=9.76%, N=1.49%.

EXAMPLE 12

2-Deoxy-3-O-{(2RS)-2-dodecylhexadecanoyl}-4,6-O-hydroxyphosphoryl-2-{(3R)-3-hydroxytetradecanamido}-D-glucopyranose; (Compound L)

The seventh step

Compound L was obtained in the same manner as that for compound K, with the exception that 2-deoxy-3-O-{(2RS)-2-dodecylhexadecanoyl}-2-{(3R)-3-hydroxytetradecanamido}-4-O-phosphono-D-glucopyranose (7l) which can be produced in the manner disclosed in Japanese Patent Disclosure No. 25494/90 was used.

m. p.: 167°-169° C.

IR(KBr)cm⁻¹: 3400, 2930, 2850, 1720, 1640, 1550.

C₄₈H₉₃NO₁₁P (891.24) theoretical value: C=64.69%, H=10.52%, N=1.57%; actual value: C=64.65%, H=10.29%, N=1.82%.

EXAMPLE 13

2-Deoxy-4,6-O-hydroxyphosphoryl-2-{(3R)-3-hydroxytetradecanamido}-3-O-{(3R)-3-tetradecanoyloxytetradecanoyl}-D-glucopyranose; (Compound M)

The seventh step

Compound M was obtained in the same manner as that for compound K, with the exception that 2-deoxy-2-{(3R)-3-hydroxytetradecanamido}-4-O-phosphono-3-O-{(3R)-3-tetradecanoyloxytetradecanoyl}-D-glucopyranose (7m) which can be produced in the manner disclosed in Japanese Disclosure No. 62889/90 was used.

[α]D: —2.0° (c=0.5, CHCl₃:MeOH=1.1).

m. p.: 168°-170° C.

C₄₈H₈₉NO₁₂P (903.32) theoretical value: C=63.83%, H=9.93%, N=1.55%, actual value: C=63.82%, H=10.02%, N=1.33%.

EXAMPLE 14

2-Deoxy-4,6-O-hydroxyphosphoryl-2-{(3R)-3-hydroxytetradecanamido}-3-O-{(3RS)-3-undecylheptadecanoyl}-D-glucopyranose; (Compound N)

The seventh step

Compound N was obtained in the same manner as that for compound K, with the exception that 2-deoxy-2-{(3R)-3-hydroxytetradecanamido}-4-O-phosphono-3-O-{(3RS)-3-undecylheptadecanoyl}-D-glucopyranose (7n) which can be produced in the manner disclosed in Japanese Patent No. 241866/89 was used.

m. p.: 176°-179° C.

C₄₈H₉₁NO₁₀P (873.23) theoretical value: C=66.02%, H=10.50%, N=1.60%; actual value: C=66.20%, H=10.24%, N=1.89%.

We claim:

1. A 4,6-O-hydroxyphosphoryl-glucosamine compound of formula (i), or a pharmaceutically-acceptable salt thereof:

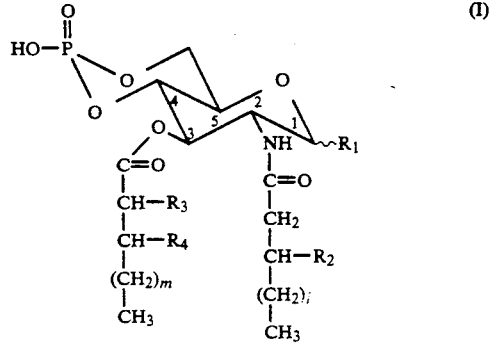

wherein R₁ and R₂ represent a hydrogen atom or a hydroxy group; one of R₃ and R₄ represents —OCO(CH₂)ₙCH₃, —CH₂(CH₂)ₙCH₃, or —O—CH$_2$(CH$_2$)$_n$CH$_3$, and the other represents a hydrogen atom; l is an integer from 4–16; m is an integer from 4–16; and n is an integer from 6–18.

2. The compound of claim 1, wherein said pharmaceutically acceptable salt is a member selected from the group consisting of an inorganic alkali metal salt, an alkali-earth metal salt, and an organic amine salt.

3. The compound of claim 1, wherein said pharmaceutically acceptable salt is a salt of said compound with sodium, potassium, lithium, calcium, triethanolamine, diethanolamine, monoethanolamine, or triethylamine.

4. The compound of claim 1, wherein said compound is a stereoisomer thereof.

5. The compound of claim 1, wherein said compound is a member selected from the group consisting of
1,5-Anhydro-2-deoxy-4,6-O-hydroxyphosphoryl-2-{(3R)-3-hydroxytetradecanamido}-3-O-{(2R)-2-tetradecanoyloxytetradecanoyl}-D-glucitol,
1,5-Anhydro-2-deoxy-3-O-{(2RS)-2-dodecanoyloxyhexadecanoyl}-2-{(3R)-3-hydroxydodecanamido}-4,6-O-hydroxyphosphoryl-D-glucitol,
1,5-Anhydro-2-deoxy-3-O-{(2RS)-2-hexadecanoyloxydodecanoyl}-2-{(3RS)-3-hydroxyhexadecanamido}-4,6-O-hydroxyphosphoryl-D-glucitol,
1,5-Anhydro-2-deoxy-3-O-{(2RS)-2-dodecanoyloxyhexadecanoyl}-4,6-O-hydroxyphosphoryl-2-{(3R)-3-hydroxytetradecanamido}-D-glucitol,
1,5-Anhydro-2-deoxy-3-O-{(2RS)-2-dodecanoyloxyhexadecanoyl}-2-{(3R)-3-hydroxydodecanamido}-4,6-O-hydroxyphosphoryl-D-glucitol,
1,5-anhydro-3-O-{(2RS)-2-decyloctadecanoyl}-2-deoxy-2-{(3RS)-3-hydroxyhexadecanamido}-4,6-O-hydroxyphosphoryl-D-glucitol,
1,5-Anhydro-2-deoxy-4,6-O-hydroxyphosphoryl-2-{(3R)-3-hydroxytetradecanamido}-3-O-{(3R)-3-tetradecanoyloxytetradecanoyl}-D-glucitol,
1,5-Anhydro-2-deoxy-4,6-O-hydroxyphosphoryl-2-{(3R)-3-hydroxytetradecanamido}-3-O-{(3R)-3-undecylheptadecanoyl}-D-glucitol,
1,5-Anhydro-2-deoxy-3-O-(2-dodecyltetradecanoyl)-4,6-O-hydroxyphosphoryl-2-tetradecanamido-D-glucitol,
1,5-Anhydro-2-deoxy-4,6-O-hydroxyphosphoryl-2-{(3R)-3-hydroxytetradecanamido}-3-O-{(3RS)-3-tetradecanoyloxytetradecanoyl}-D-glucitol,
2-deoxy-4,6-O-hydroxyphosphoryl-2-{(3R)-3-hydroxytetradecanamido}-3-O-{(2RS)-tetradecanoyloxytetradecanoyl}-D-glucopyranose,
2-Deoxy-3-O-{(2RS)-2-dodecylhexadecanoyl}-4,6-O-hydroxyphosphoryl-2{(3R)-3-hydroxytetradecanamido}-D-glucopyranose,
2-Deoxy-4,6-O-hydroxyphosphoryl-2-{(3R)-3-hydroxytetradecanamido}-3-O-{(3R)-3-tetradecanoyloxytetradecanoyl}-D-glucopyranose,
2-Deoxy-4,6-O-hydroxyphosphoryl-2-{(3R)-3-hydroxytetradecanamido}-3-O-{(3RS)-3-undecylheptadecanoyl}-D-glucopyranose,
1,5-Anhydro-2-deoxy-2-dodecanamido-3-O-{(2RS)-2-hexadecyloxydodecanoyl}-4,6-O-hydroxyphosphoryl-D-glucitol,
1,5-Anhydro-2-deoxy-2-dodecanamido-3-O-{(3RS)-3-hexadecyloxydodecanoyl}-4,6-O-hydroxyphosphoryl-D-glucitol,
1,5-Anhydro-2-deoxy-3-O-{(3RS)-3-dodecylhexadecanoyl}-2-hexadecanamido-4,6-O-hydroxyphosphoryl-D-glucitol,
1,5-Anhydro-2-deoxy-3-O-{(2RS)-2-dodecylhexadecanoyl}-2-{(3R)-3-hydroxydodecanamido}-4,6-O-hydroxyphosphoryl-D-glucitol,
1,5-anhydro-3-O-{(3RS)-3-decyloctadecanoyl}-2-deoxy-2-{(3RS)-3-hydroxyhexadecanamido}-4,6-O-hydroxyphosphoryl-D-glucitol,
1,5-anhydro-2-deoxy-2-dodecanamido-3-O-{(2RS)-2-hexadecyloxydodecanoyl}-4,6-O-hydroxyphosphoryl-D-glucitol,
1,5-anhydro-3-O-{(3RS)-3-decyloctadecanoyl}-2-deoxy-2-hexadecanamido)-4,6-O-hydroxyphosphoryl-D-glucitol,
2-deoxy-3-O-{(2RS)-2-dodecylhexadecanoyl}-4,6-O-hydroxyphosphoryl-2-tetradecanamido-D-glucopyranose,
2-deoxy-4,6-O-hydroxyphosphoryl-2-tetradecanamido-3-O-{(2RS)-2-tetradecanoyloxytetradecanoyl}-D-glucopyranose,
2-deoxy-3-O-{(2RS)-2-dodecyloxyhexadecanoyl}-4,6-O-hydroxyphosphoryl-2-tetradecanamido-D-glucopyranose,
2-deoxy-3-O-{(3RS)-3-dodecyloxyhexadecanoyl}-4,6-O-hydroxyphosphoryl-2-tetradecanamido-D-glucopyranose,
2-deoxy-4,6-O-hydroxyphosphoryl-2-tetradecanamido-3-O-{(3RS)-3-tetradecanoyloxytetradecanoyl}-D-glucopyranose,
2-deoxy-3-O-{(3RS)-3-dodecyloxyhexadecanoyl}-4,6-O-hydroxyphosphoryl-2-tetradecanamido-D-glucopyranose, and
2-deoxy-3-O-{(3RS)-3-dodecyloxyhexadecanoyl}-2-{(3RS)- 3-hydroxyoctadecanamido}-4,6-O-hydroxyphosphoryl-D-glupyranose.

6. A pharmaceutical composition, comprising at least one compound of claim 1 and at least one inert diluent or dispersing agent.

* * * * *